US006087346A

United States Patent [19]
Glennon et al.

[11] Patent Number: 6,087,346
[45] Date of Patent: Jul. 11, 2000

[54] SIGMA RECEPTOR LIGANDS AND THE USE THEREOF

[75] Inventors: Richard A. Glennon, Richmond, Va.; James B. Fischer, Medford, Mass.

[73] Assignees: Cambridge Neuroscience, Inc., Cambridge, Mass.; Virginia Commonwealth University, Richmond, Va.

[21] Appl. No.: 08/564,362

[22] PCT Filed: Jun. 23, 1994

[86] PCT No.: PCT/US94/07121

§ 371 Date: Feb. 21, 1996

§ 102(e) Date: Feb. 21, 1996

[87] PCT Pub. No.: WO95/00131

PCT Pub. Date: Jan. 5, 1995

Related U.S. Application Data

[63] Continuation-in-part of application No. 08/082,406, Jun. 23, 1993, abandoned, which is a continuation of application No. PCT/US94/07121, Jun. 25, 1994.

[51] Int. Cl.⁷ ............................ A01N 65/00; A01N 33/02; C07C 221/00; C07D 217/00
[52] U.S. Cl. ........................... 514/65; 514/649; 514/651; 514/655; 546/139; 546/141; 546/149; 546/164; 546/176; 564/342; 564/344; 564/345; 564/381; 564/383
[58] Field of Search .................. 514/649, 651, 514/65, 655; 564/342, 344, 345, 383, 381

[56] References Cited

U.S. PATENT DOCUMENTS

| | | | |
|---|---|---|---|
| 2,313,016 | 3/1943 | Hornstein et al. | 260/472 |
| 2,649,444 | 8/1953 | Barrett et al. | |
| 2,843,593 | 7/1958 | Farkas et al. | 260/294.3 |
| 3,122,555 | 2/1964 | Janssen et al. | |
| 3,256,278 | 6/1966 | Petracek et al. | 260/247.5 |
| 3,864,501 | 2/1975 | Yokoyama et al. | 426/268 |
| 4,339,384 | 7/1982 | Maillard et al. | 548/525 |
| 4,866,062 | 9/1989 | Toth et al. | 514/255 |
| 4,866,076 | 9/1989 | Gribble | 514/307 |
| 4,873,262 | 10/1989 | Junge et al. | 514/510 |
| 4,943,428 | 7/1990 | Lucot et al. | 424/10 |
| 4,962,107 | 10/1990 | Nakamura et al. | 514/237.5 |
| 4,962,115 | 10/1990 | Van Daele | 514/326 |
| 5,109,002 | 4/1992 | Cain et al. | 514/256 |

FOREIGN PATENT DOCUMENTS

| | | |
|---|---|---|
| 0064964 | 11/1982 | European Pat. Off. |
| 0 272 534 | 6/1988 | European Pat. Off. |
| 0286278 | 10/1988 | European Pat. Off. |
| 0296560 | 12/1988 | European Pat. Off. |
| 0372776 | 6/1990 | European Pat. Off. |
| 0386997 | 9/1990 | European Pat. Off. |
| 1421208 | 12/1965 | France . |
| 4274 | 8/1966 | France . |
| 25 06 770 | 9/1975 | Germany . |
| 966943 | 8/1964 | United Kingdom . |
| 1109924 | 4/1968 | United Kingdom . |
| 1184023 | 3/1970 | United Kingdom . |
| WO 81/03491 | 12/1981 | WIPO . |
| WO 88/03756 | 6/1988 | WIPO . |
| WO 90/15047 | 12/1990 | WIPO . |
| WO 91/09594 | 7/1991 | WIPO . |
| WO 93/00313 | 1/1993 | WIPO . |

OTHER PUBLICATIONS

R. Glennon et al., *Med. Chem. Res.*, 1(3):207–212 (1991).
M. El–Ashmawy et al.,*Med. Chem. Res.*, 2(2):119–126 (1992).
Database Crossfire, Beilstein Informationsgesellschaft GmbH, XP002010566.
R. Neale et al., *Journal of Organic Chemistry*, 30:3683–3688 (1965).
B. Hasiak, *Bulletin de la Societe Chimique de France*, No. 9–10, pp. 1531–36 (1976).
R. Glennon et al.,, *Journal of Medicinal Chemistry*, 37(8):1214–1219 (1994).
J. Junien et al., *Gastroenterology*, 99(3):684–689 (1990).
X. Pascaud et al., *The Journal of Phamacology and Experimental Therapeutics*, 255(3):1354–1359 (1990).
J. Walker et al., *Pharmacological Reviews*, 42(4):355–402 (1990).
S. Snyder et al., *The Journal of Neuropsychiatry and Clinical Neurosciences*, 1(1);7–15 (1989).
J. Cymerman–Craig et al., *Chemical Abstracts*, 54:2280a.
R.K. Raghupathi et al., *J. Med. Chem.*, 34:2633–2638 (1991).
R.A. Glennon et al., *Pharmacol. Biochem. Behav.*, 40:1009–1017 (1991).
R.A. Glennon et al., *J. Med. Chem.*, 34:1855–1859 (1991).
R.A. Glennon et al., *J. Med. Chem.*, 34:1094–1098 (1991).
R.A. Glennon et al., *Pharmacol. Biochem. Behav.*, 37:557–559 (1990).
R.A. Glennon et al., *NIOA Res. Monogr.*, 94:Pharmacol. Toxicol. Amphetamine Relat. Des. Drugs, pp. 43–67 (1989).
R.A. Glennon et al., *ACS Symp. Ser.*, 413:264–280 (1989).
R.A. Glennon et al., *Pharmacol. Biochem. Behav.*, 33:909–912 (1989).
R.A. Glennon et al., *J. Med. Chem.*, 32:1921–1926 (1989).
R.A. Glennon et al., *Drug Dev. Res.*, 16:335–343 (1989).
R.A. Glennon et al., *J. Med. Chem.*, 31:867–870 (1988).
R.A. Glennon et al., *Pharmacol. Biochem. Behav.*, 29:197–199 (1988).
International Search Report for PCT Application No. PCT/US90/07653.

(List continued on next page.)

*Primary Examiner*—John Kight
*Assistant Examiner*—Raymond Covington
*Attorney, Agent, or Firm*—Peter F. Corless; Christine C. O'Day; Dike, Bronstein, Roberts & Cushman, LLP

[57] ABSTRACT

The invention relates to methods for the treatment of central nervous system disorders, neurological disorders, gastrointestinal disorders, drug abuse, angina, migraine, hypertension and depression by administering a pharmaceutical composition comprising an effective amount of certain sigma receptor ligands to a patient in need of such treatment. The invention further relates to novel sigma receptor ligands having high binding to the sigma receptor and pharmaceutical compositions thereof.

17 Claims, No Drawings

OTHER PUBLICATIONS

S. Glozman et al., "Synthesis of Certain 2-Acyl-4-Methylphenols", pp. 212-214.
P. Janssen et al., *Journal of Medicinal and Pharmaceutical Chemistry*, 2(3):271–280 (1960).
R. Young et al., *Med. Res. Rev.*, 6(1):99–130 (1986).
R.A. Glennon et al., *Pharmacol. Biochem. Behav.*, 21:895–901 (1984).
R.A. Glennon et al., *Psychopharmacol. Bull.*, 22(3):953–958 (1986).
S.J. Peroutka, *J. Neurochem.*, 47(2):529–540 (1986).
B.A. Faraj et al., *J. Med. Chem.*, 19(1):20–25 (1976).
R.A. Lyon et al., *J. Med. Chem.*, 29:630–634 (1986).
J. Klosa et al., *Chem. Abstr.*, 63:11579b (1965).
R.A. Glennon et al., *J. Med. Chem.*, 34:3360–3365 (1991).
M.A. Vitolinya, *Chem. Abstr.*, 72:65176t (1970).
R.N. Prasad et al., *Chem. Abstr.*, 70:11676w (1969).
T.P. Su, *Neurosci. Lett.*, 71:224–228 (1986).
J.M. Beaton et al., *Nature*, 220:800–801 (1968).
R.W. Fuller et al., *J. Pharmacol. Exp. Therapeut.*, 184(1):278–284 (1973).
R.W. Fuller et al., *Neuropharmacol.*, 13:609–614 (1974).
H.E. Smith et al., *J. Org. Chem.*, 40(11):1562–1567 (1975).
R.S. Sloviter et al., *Pharmacol. Biochem. Behav.*, 13:283–286 (1980).
G. Pala et al., *J. Med. Chem.*, 13(4):668–671 (1970).
H. Van de Waterbeemd et al., *J. Med. Chem.*, 30:2175–2181 (1987).
M. Freifelder et al., *Chem. Abstr.*, 61:14559g (1964).
A.P. Tazelaar et al., *Chem. Abstr.*, 39:11322b (1962).
N. Busch et al., *Chem. Abstr.*, 70:20085e (1969).
R.Y. Mauvernay, *Chem. Abstr.*, 66:55520h (1967).
A. Krotowska et al., *Chem. Abstr.*, 108:87584p (1988).
U. Hacksell et al., *J. Med. Chem.*, 22(12):1469–1475 (1979).
J.D. McDermed et al., *J. Med. Chem.*, 18(4):362–367 (1975).
R.A. Glennon et al., *Chem. Abstr.*, 102:105731s (1985).
M. Beaulieu et al., *Eur. J. Pharmacol.*, 105:15–21 (1984).
N. Naiman et al., *J. Med. Chem.*, 32:253–256 (1989).
B.L. Largent et al., *Mol. Pharmacol.*, 32:772–784 (1987).
R.A. Beecroft et al., *Tetrahedron*, 41 (18):3853–3865 (1985).
R.W. Fuller et al., *Res. Commun. Chem. Pathol. Pharmacol.*, 29(1):201–204 (1980).
J. Boissier et al., *Chem. Abstr.*, 61:10691c (1961).
Roessler, *Chem. Abstr.*, 61:13328g (1961).
H. Ruschig et al., *Chem. Abstr.*, 52:3253e (1959).
V.I. Shvedov et al., *Chem. Abstr.*, 73;119806q (1970).
D. Popov, *Chem. Abstr.*, 67:54102m (1967).
R.A. Glennon et al., *J. Med. Chem.*, 31:1968–1971 (1988).
R.N. Prased et al., *J. Med. Chem.*, 111144–1150 (1968).
B.L. Largent et al., *Eur. J. Pharmacol.*, 155:345:347 (1988).
R.A. Glennon et al., *Pharmacol. Biochem, Behav.*, 17:603–607 (1982).
R.A. Glennon et al., *J. Med. Chem.*, 25:68–70 (1982).
R.A. Glennon et al., *Eur. J. Pharmacol.*, 154:339–341 (1988).
L.E. Arvidsson et al., *Prog. Drug. Res.*, 30:365–471 (1986).
R.A. Glennon et al., *J. Med. Chem.*, 24:678–683 (1981).
R.A. Glennon et al., *Life Sciences*, 35:1475–1480 (1984).
R. Glennon, *J. Medicinal Chemistry*, 30(1):1–12 (1987).
Samant et al., *J. Indian Chemical Society*, 56 (10):1002–1005 (1979).
"Merck Index", pp. 218 and 725 (1987).
Chemical Abstracts 56, Abstract No. 1324f "Mechanism of chemical reactions"(1962).
Chemical Abstracts 54, Abstract No. 22430h (1960).
Chemical Abstracts 60, Abstract No. 12028d (1964).
Anderson et al., *J. Medicinal Chemistry*, 19(11):1270–1275 (1976).
Sharkey et al., *Eur. J. Pharmacol.*, 149: 171–174 (1988).
D.T. Manallack et al., *Eur. J. Pharmacol.*, 144:231–235 (1987).
R.W. Fuller et al., *J. Med. Chem.*, 14:322–325 (1971).
W.O. Foye et al., *J. Pharm. Sci.*, 68:591–595 (1979).
J.R. Boissier et al., *Chem. Abstr.*, 66:46195h (1967).
J.R. Boissier et al., *Chem. Abstr.*, 67:21527a (1967).
J.M. Osbond et al., *Chem. Abstr.*, 69:51816c (1968).
T. Gosztonyi et al., *J. Label. Comp. Radiopharm.*, 13(3):293–303 (1977).
R.T. Coutts et al., *Can. J. Microbiol.*, 26:844–849 (1980).
R.A.B. Aldous, *J. Med. Chem.*, 17(10):1100–1111 (1974).
R.W. Fuller et al., *J. Pharm. Pharmacol.*, 25:828–829 (1973).
R.W. Fuller et al., *Neuropharmacology*, 14:739–746 (1975).
S. Conde et al., *J. Med. Chem.*, 21(9):978–981 (1978).
I. Lukovits, *Int. J. Quantum Chem.*, 20:429–438 (1981).
B. Law, *J. Chromatog.*, 407:1–18 (1987).
A.M. Johansson et al., *J. Med. Chem.*, 30:602–611 (1987).
Gray et al, Chemical Abstract vol. 113 No. 91246 Amhistamine interact with central nervous system, 1990.
Glennon, Chemical Abstract vol. 115 No. 182801 "Prep. of sub. Phenyl–isoprogylomine and analog as signs recepts liguid for test. of schzophen & propdo", 1989.
Anderson et al. Chem Abstract vol. 85, No. 137895 "Phenylalanx Trafe ubonuiler and synthetas",1976.

SIGMA RECEPTOR LIGANDS AND THE USE THEREOF

This application is a continuation-in-part of U.S. app. Ser. No. 08/082,406 (abandoned) filed Jun. 23, 1993 which is a continuation of PCT/US94/07121 filed Jun. 25, 1994.

The present application is a continuation-in-part of U.S. application Ser. No. 08/082,406 filed on Jun. 23, 1993, which is a continuation-in-part of U.S. application Ser. No. 07/894,771, filed on Jun. 10, 1992, and U.S. application Ser. No. 07/720,173, filed on Jun. 27, 1991, all of said prior U.S. applications being incorporated herein by reference.

FIELD OF THE INVENTION

The invention is in the field of medicinal chemistry. In particular, the invention relates to new compounds having high binding to the sigma receptor and pharmaceutical compositions thereof. These compounds are useful for the treatment of central nervous system disorders, neurological disorders and other conditions.

BACKGROUND OF THE INVENTION

Brain sigma receptors are the subject of intense investigation in light of the fact that sigma receptors bind many psychotropic drugs (Sonders et al., *Trends Neurosci.*, 1: 37–40 (1988)). Moreover, certain sigma receptor ligands have antipsychotic activity which suggests that sigma receptor active compounds may be used for the treatment of schizophrenia (Largent et al., *Eur. J. Pharmacol.*, 11: 345–347 (1988)).

Certain neuroleptic (i.e., antipsychotic) agents bind with very high affinity at sigma sites. Su, T., *J. Pharmacol. Exp. Ther.*, 223: 284 (1982); Tam, S. W., *Proc. Nat. Acad. Sci (USA)*, 80: 6703 (1983). One agent with very high affinity for sigma sites (Ki ca 1 nM; i.e., approximately 100-fold higher affinity than N-allyl normetazocine (NANM) is the neuroleptic agent haloperidol. Tam, S. W., et al., *Proc. Nat. Acad. Sci (USA)*, 81: 5618 (1984). Sigma-opiates, such as NANM, bind with low affinity at typical opiate receptors but bind with significant affinity at PCP receptors.

Current neuroleptic agents are thought to produce their effects via a dopaminergic (DA) mechanism; they display very high affinities for DA binding sites. However, not all of the potent neuroleptic agents bind at [$^3$H]NANM-labelled sigma sites, nor do the sigma-opiates bind at DA sites. This has led to the suggestion that the sites labelled by [$^3$H] NANM be termed sigma-sites and not sigma-opiate sites (i.e., it may simply be coincidental that the sigma opiates possess an opiate-like chemical structure). In addition, there has been speculation that agents with high affinity for sigma sites may either (a) produce psychotic effects (if they behave as agonists), or (b) produce antipsychotic effects (if they behave as antagonists). It has further been speculated that certain neuroleptic agents, such as haloperidol, produce their antipsychotic effects by both a sigma and DA mechanism. Tam, S. W. and Cook, L., *Proc. Nat. Acad. Sci. (USA)*, 81: 5618 (1984). In fact, [$^3$H]haloperidol, in combination with spiperone (an agent with high affinity for DA sites and essentially no affinity for sigma sites) is now commonly used to label sigma sites in radioligand binding studies.

A number of researchers have studied the structure-activity relationship of sigma ligands. For example, Manallack, D. T., et al., *Eur. J. Pharmacol.*, 144: 231–235 (1987), disclose a receptor model for the phencyclidine and sigma binding sites. Manallack et al. disclose that in a recent SAR study (Largent et al., in press), sigma site affinity was shown to be enhanced by large N-alkyl substituents, e.g., benzyl or phenylethyl.

Largent, B. L., et al., *Mol. Pharmacol.*, 32: 772–784 (1987), disclose a study of the structural determinants of sigma receptor affinity. In particular, Largent et al. teach that several piperidine and piperazine derivatives have sigma receptor activity. Largent et al. also disclose that affinity for the sigma receptor is markedly influenced by the N-alkyl substituents, with more lipophilic substituents affording greater affinity for the sigma receptor binding sites.

Sharkey, J., et al., *Eur. J. Pharmacol.*, 149: 171–174 (1988), studied the sigma receptor binding activity of cocaine-related compounds.

The literature contains a number of suggestions that the sigma receptor is not a single, homogeneous binding site. Bowen, W. D. et al., *Eur. J. Pharm.*, 163: 309–318 (1989), disclose that the effect of U.V. radiation on sigma receptor binding depended on the radioligand used to assay for it. It was also demonstrated that the binding characteristics of several sigma ligands were different in membranes from certain cell lines than in guinea pig brain membranes. (Hellewell, S. B. and Bowen, W. D., *Brain Res.*, 527: 224–253 (1990); Wu, X. Z. et al., *J. Pharmacol. Exp. Ther.*, 257: 351–359 (1991)). At least two groups have reported significantly different pharmacology for "sigma receptors" when using different radioligands to label these sites. (Itzhak, Y., et al., *J. Pharmacol. Exp. Ther.*, 257: 141–148 (1991); Karbon, E. W., et al., *Eur. J. Pharm.*, 93: 21–27 (1991)). In addition, [$^3$H]DTG binding was found to have two components in guinea pig membranes (Rothman, R. B. et al., *Mol. Pharm.*, 39: 222–232 (1991)). An overlap of sigma sites with some of the multiple sites labeled by [$^3$H]dextromethorphan has also been described (Musacchio, J. M., et al., *Life Sci.*, 45: 1721–1732 (1989)).

Hellewell and Bowen, *Brain Res.*, 527: 224–253 (1990), were the first to define the characteristics of the two putative sigma receptor subtypes, named sigma-1 and sigma-2. The primary pharmacological distinction between these two sites is the affinity of the (+) isomers of the benzomorphan opiates for the binding sites. These compounds, such as (+)SKF 10,047 (NANM) and (+)pentazocine show nearly two orders of magnitude higher affinity for the sigma-1 site compared to the sigma-2 site. The (−) isomers of the benzomethorphans show little selectivity between these two sites. Other distinctions noted between the two sites are a preponderance of the sigma-2 sites in cell lines such as NCB-20, PC12 and NG108-15 cells (Hellewell, S. B. and Bowen, W. D., *Brain Res.*, 527: 224–253 (1990); Wu, X. -Z., et al., *J. Pharmacol. Exp. Ther.*, 257: 351–359 (1991); George, A. and Friedl, A., *J. Pharmacol. Exp. Ther.*, 259: 479–483 (1991); Quirion, R., et al., *Trends in Pharmacological Sciences*, 13: 85–86 (1992)).

There has been considerable research on amphetamine and amphetamine derivatives which were not examined for sigma receptor activity (nor are they believed to possess much of such activity). See, e.g., Aldous, F. A. B., *J. Med. Chem.*, 17: 1100–1111 (1974); Fuller, R. W. et al., *J. Med. Chem.*, 14: 322–325 (1971); Foye, W. O. et al., *J. Pharm. Sci.*, 68: 591–595 (1979); Boissier, J. R. et al., *Chem. Abstr.*, 66: 46195h (1967); Boissier, J. R. et al., *Chem. Abstr.*, 67: 21527a (1967); Osbond, J. M. et al., *Chem. Abstr.*, 69: 51816c (1968); Gosztonyi, T. et al., *J. Label. Comp. Radiopharm.*, 8: 293–303 (1977); Coutts, R. T. et al, *Can. J. Microbiol.*, 26: 844–848 (1980); Fuller, R. W. et al., *J. Pharm. Pharmacol.* 25: 828–829 (1973); Fuller, R. W. et al., *Neuropharmacology*, 14: 739–746 (1975); Conde, S. et al., J. Med. Chem., 21: 978–981 (1978); Lukovits, I., Int. J. Quantum. Chem., 20: 429–438 (1981); Law, B., J. Chromatog., 407: 1–18 (1987); Johansson, A. M. et al., J. Med. Chem., 30: 602–611 (1987); Hacksell, U. et al., J. Med. Chem., 22: 1469–1475 (1979); McDermed, J. D. et al., J. Med. Chem., 18: 362–367 (1975); Glennon, R. A. et al, Pharmacol. Biochem. Behav., 21: 895–901 (1984); Beaulieu, M. et al., Eur. J. Pharmacol., 105: 15–21 (1984); Naiman, N. et al., J. Med. Chem., 32: 253–256 (1989); Beecroft, R. A. et al., Tetrahedron, 41: 3853–3865 (1985); Fuller, R. W., et al., J. Pharmacol. Exp. Therapeut., 218: 636–641 (1981); Fuller, R. W. et al., Res. Commun. Chem. Pathol. Pharmacol., 29: 201–204 (1980); Boissier, J. et al., Chem. Abstr., 61: 10691 c; Roessler, Chem Abstr., 61: 13328g; Ruschig, H., et al., Chem. Abstr., 53: 3253e; Shvedov, V. I., et al., Chem. Abstr., 73: 11806q (1970); Popov, D., Chem. Abstr., 67: 54102m (1967); Glennon, R. A et al., J. Med. Chem., 31: 1968–1971 (1988); and Prasad, R. N et al., J. Med. Chem., 11: 1144–1150 (1968). These documents are discussed in WO 93/00313, publication date Jan. 7, 1993, which corresponds to U.S. application Ser. No. 07/894,771. See also WO 91/09594.

Despite the development of the above-mentioned compounds, the need continues to exist for new sigma receptor ligands and for methods for the treatment of central nervous system disorders and other conditions, utilizing such ligands.

SUMMARY OF THE INVENTION

The present invention relates to the discovery of certain compounds that exhibit affinity for the sigma receptor including certain phenylalkyl-amine, aminotetralin, piperazine, piperidine and related compounds that have high binding to the sigma receptor.

In addition, the present invention relates to methods of treating patients suffering from central nervous system disorders, drug abuse, gastrointestinal disorder(s), hypertension, migraine, angina and/or depression, which comprises administering to said patient a therapeutically effective amount of one or more compounds selected from Formulae I, II, III, IV, and V as defined below.

The invention also provides methods of treating patients suffering from or susceptible to neurological disorders that comprise administering to such a patient one or more compounds selected from Formulae I, II, III, IV, and V as defined below.

The present invention also relates to certain novel sigma receptor ligands, including those defined by Formulae I, II, III, IV, and V, and pharmaceutically acceptable salts of such compounds, as well as pharmaceutical compositions comprising one or more compounds of Formulas I, II, II, IV or V, or pharmaceutically accecptable salts thereof.

Formula I:

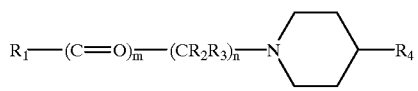

wherein m is 0 or 1; n is 0, 1, 2, 3, 4, 5, or 6; $R_1$ is selected from $C_{1-6}$ alkyl, $C_{3-6}$ cycloalkyl, phenyl, substituted phenyl, naphthyl, substituted naphthyl, indane, substituted indane, tetralin, substituted tetralin, benzocycloheptane, substituted benzocycloheptane, wherein the substituents are selected from $C_{1-6}$ alkyl, $C_{1-6}$ alkoxy, halogen, hydroxy, $C_{1-6}$ alkyl, trifluoromethyl, and the like (as defined below). In the alternative, $R_1$ may be:

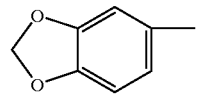

$R_2$ and $R_3$ are each independently selected from hydrogen, hydroxy, $C_{1-6}$ alkyl, or together two $R_2$ and $R_3$ groups may be a double bond between adjacent carbon atoms, etc. $R_4$ is hydrogen, $C_{1-6}$ alkyl, substituted $C_{1-6}$ alkyl, benzyl, $C_{2-6}$ alkaryl, benzoyl, phenyl, substituted phenyl, naphthyl, substituted naphthyl, indane, substituted indane, tetralin, substituted tetralin, benzocycloheptane, substituted benzocycloheptane, wherein the substituents are selected from halogen, hydroxy, $C_{1-6}$ alkyl, and the like (as defined below). In the alternative, $R_4$ may be:

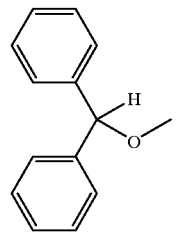

Formula II:

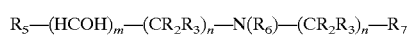

$$R_5-(HCOH)_m-(CR_2R_3)_n-N(R_6)-(CR_2R_3)_n-R_7$$

wherein m, n, $R_2$ and $R_3$ are defined as above, $R_6$ is selected from hydrogen and $C_{16}$ alkyl; $R_5$ and $R_7$ are each independently selected from the group consisting of; $C_{1-6}$ alkyl, substituted $C_{1-6}$ alkyl, benzyl, substituted benzyl, phenyl, substituted phenyl, benzoyl, substituted benzoyl, naphthyl, substituted naphthyl, indane, substituted indane, tetralin, substituted tetralin, benzocycloheptane, substituted benzocycloheptane, wherein the substituents are selected from $C_{1-6}$ alkyl, $C_{1-6}$ alkoxy, halogen, hydroxy, sulfo ($-SO_3H$), trifluoromethyl, and the like (as defined below). In the alternative, $R_5$ may be selected from the following:

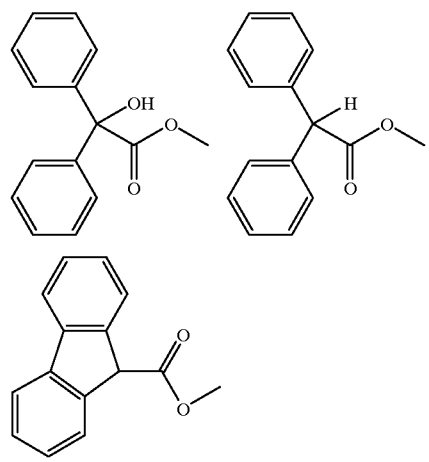

Formula III:

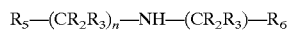

$$R_5-(CR_2R_3)_n-NH-(CR_2R_3)-R_6$$

wherein n, $R_2$, $R_3$, $R_5$ and $R_6$ are defined as above.

Formula IV:

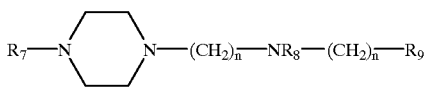

wherein n, m and $R_7$ are each defined as above; $R_8$ is selected from the group consisting of hydrogen, $C_{1-6}$ alkyl, acetyl, and the like; and wherein $R_9$ is selected from the group consisting of hydrogen, $C_{1-6}$ alkyl, substituted $C_{1-6}$ alkyl, benzyl, substituted benzyl, phenyl, substituted phenyl, benzoyl, substituted benzoyl, naphthyl, substituted naphthyl, indane, substituted indane, tetralin, substituted tetralin, benzocycloheptane, substituted benzocycloheptane, wherein the substituents are selected from $C_{1-6}$ alkyl, $C_{1-6}$ alkoxy, halogen, hydroxy, sulfo (—$SO_3H$), trifluoromethyl, and the like (as defined below).

Formula V:

wherein n and m are defined as above; each Ar is independently benzyl, substituted benzyl, phenyl or substituted phenyl, naphthyl, substituted naphthyl, indane, substituted indane, tetralin, substituted tetralin, benzocycloheptane, substituted benzocycloheptane, and Het is heterocyclic ring having 1 or 2 nitrogen atoms, and from 3 to 8 carbon atoms, as well as from 0 to 3 double bonds, which may likewise be further substituted with $C_{1-6}$ alkyl, $C_{1-6}$ alkylamino, hydroxy, halogen, and other substituents as defined below.

The invention further provides compounds of the following Formula VI:

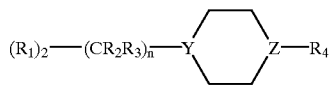

wherein $R_1$, $R_2$, $R_3$, $R_4$ and n are each as defined above for Formula I, or $R_1$ is further independently selected from

and wherein Y and Z are each independently a nitrogen or carbon (i.e., CH or $CH_2$), and preferably one of Y or Z is nitrogen and the other is carbon; and pharmaceutically acceptable salts thereof.

The invention also provides compounds of the following Formula VII:

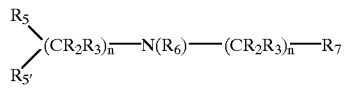

wherein each $R_2$, $R_3$, $R_6$, $R_7$ and n are as defined above for Formula II, and $R_5$ and $R_{5'}$ are independently hydrogen or $C_{1-6}$ alkyl, substituted $C_{1-6}$ alkyl, benzyl, substituted benzyl, phenyl, substituted phenyl, benzoyl, substituted benzoyl, 1,2,3,4-tetrahydronaphthalene, substituted 1,2,3,4-tetrahydronaphthalene, 5,6,7,8-tetrahydroisoquinoline, substituted 5,6,7,8-tetrahydroisoquinone, 1,2,3,4-tetrahydroquinoline, and substituted 1,2,3,4-tetrahydroquinoline, wherein the substituents are selected from $C_{1-6}$ alkyl, $C_{1-6}$ alkoxy, halogen, hydroxy, sulfo(—$SO_3H$), trifluoromethyl, etc. (as defined below), and preferably at least one of $R_5$ and $R_{5'}$ is other than hydrogen, and more preferably at least one of $R_5$ and $R_{5'}$ is other than hydrogen or substituted or unsubstituted alkyl; and pharmaceutically acceptable salts thereof.

The invention also provides pharmaceutical compositions comprising one or more compounds of Formulae VI or VII, and methods for treating a mammal, particularly a human, in need of treatment for or susceptible to a central nervous system disorder, drug abuse, a gastrointestinal disorder, hypertension, migraine, angina and/or depression, which methods comprise administering to said patient a therapeutically effective amount of one or more compounds of said Formulae VI or VII.

In another aspect and as discussed above, the invention provides methods for treating a mammal, particularly a human, in need of treatment for or susceptible to a neurological disorder such as e.g. a movement disorder, epilepsy or brain or spinal cord ischemia or trauma. The methods provide administration of one or more compounds of Formulae I, II, III, IV, V, VI or VII to mammal in need of treatment for or susceptible to a neurological disorder.

In International application WO 93/0031 3 certain methods are disclosed for the treatment of a patient, particularly a human patient, suffering from a central nervous system disorder, drug abuse, a gastrointestinal disorder, hypertension, migraine, angina and/or depression, which comprises administering to said patient a therapeutically effective amount of a compound having the following Formula:

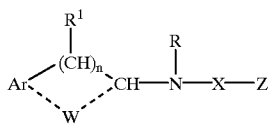

wherein:

Ar is aryl or heteroaryl, wherein the aryl or heteroaryl group can be substituted by hydrogen, halogen such as chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, $C_3$–$C_6$ heterocycloalkyl, a $C_3$–$C_6$ heterocycloalkyl ring fused to a benzene ring, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

R is hydrogen or $C_1$–$C_6$ alkyl;

each $R^1$ is selected from the group consisting of hydrogen, $C_1$–$C_6$ alkyl, hydroxy, amino, $C_1$–$C_6$ alkylamino or =O; or R and an $R^1$ group together form a morpholino ring;

n is 0–5;

W is —$(CH_2)_p$— or —H—, wherein p is 1–3;

X is selected from the group consisting of:

—(CH$_2$)$_q$—, wherein q is 1–6;

—(CH$_2$)$_r$—C≡C—(CH$_2$)$_r$—, wherein each r is 0–3 independently;

—(CH$_2$)$_r$—CH=CH—(CH$_2$)$_r$—;

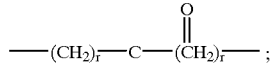

—(CH$_2$)$_r$—Y—(CH$_2$)$_r$—, wherein each said r is independently 0–3 and Y is O or S; or C$_1$–C$_6$ alkyl (wherein Z is hydrogen);

Z is hydrogen, aryl, an aryl-substituted carboxylic acid group, heteroaryl or cycloalkyl, wherein aryl, heteroaryl and cycloalkyl can be substituted by hydrogen, halogen such as chloro, fluoro, bromo, iodo; CF$_3$, C$_1$–C$_6$ alkoxy, C$_2$–C$_6$ dialkoxymethyl, C$_1$–C$_6$ alkyl, cyano, C$_3$–C$_{15}$ dialkylaminoalkyl, carboxy, carboxamido, C$_1$–C$_6$ haloalkyl, C$_1$–C$_6$ haloalkylthio, allyl, aralkyl, C$_3$–C$_6$ cycloalkyl, aroyl, aralkoxy, C$_2$–C$_6$ carboxylic acyl, aryl, substituted aryl, heteroaryl, substituted heteroaryl, C$_3$–C$_6$ heterocycloalkyl, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkylamino, C$_2$–C$_{15}$ dialkylamino, hydroxy, carbamoyl, C$_1$–C$_6$ N-alkylcarbamoyl, C$_2$–C$_{15}$ N,N-dialkylcarbamoyl, nitro, C$_2$–C$_{15}$ dialkylsulfamoyl or an ortho methylene dioxy group;

wherein said compound exhibits high binding activity with respect to the sigma receptors.

Also disclosed in said International Application are methods for treating central nervous system disorders, drug abuse, gastrointestinal disorders, hypertension, migraine, angina and depression, using compounds having the following Formula:

(XXXIII)

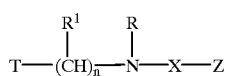

wherein T is a cycloalkyl group or Ar group as defined above, n, R, R$^1$, X and Z are as defined above, but where R and R$^1$ may together form a piperazinyl or piperazinyl ring in addition to a morpholino ring; and wherein said compound exhibits high binding activity with respect to the sigma receptors.

DETAILED DESCRIPTION OF PREFERRED EMBODIMENTS

The present inventors have now discovered novel methods for treating an animal, preferably a mammal, particularly a human, suffering from a central nervous system disorder, drug abuse, a gastrointestinal disorder, hypertension, migraine, angina and/or depression, which comprises administering to said animal a therapeutically effective amount of one or more compounds of Formula 1:

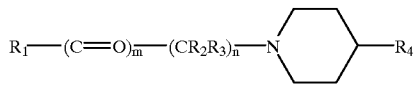

wherein m is 0 or 1; n is 0, 1, 2, 3, 4, 5, or 6; R$_1$ is selected from C$_{1-6}$ alkyl, C$_{3-6}$ cycloalkyl, phenyl, substituted phenyl, wherein the substituents are selected from C$_{1-6}$ alkyl, C$_{1-6}$ alkoxy, halogen, hydroxy, C$_{1-6}$ alkyl, trifluoromethyl, etc. In the alternative, R$_1$ may be:

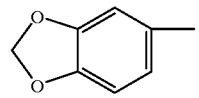

R$_2$ and R$_3$ are each independently selected from hydrogen, hydroxy, C$_{1-6}$ alkyl, or together two R$_2$ and R$_3$ groups may be a double bond between adjacent carbon atoms, etc. R$_4$ is hydrogen, C$_{1-6}$ alkyl, substituted C$_{1-6}$ alkyl, benzyl, C$_{2-6}$ alkaryl, benzoyl, phenyl, substituted phenyl, wherein the substituents are selected from halogen, hydroxy, C$_{1-6}$ alkyl, etc. In the alternative, R$_4$ may be:

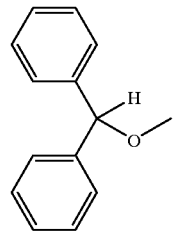

Particularly preferred compounds of Formula I include the following structures:

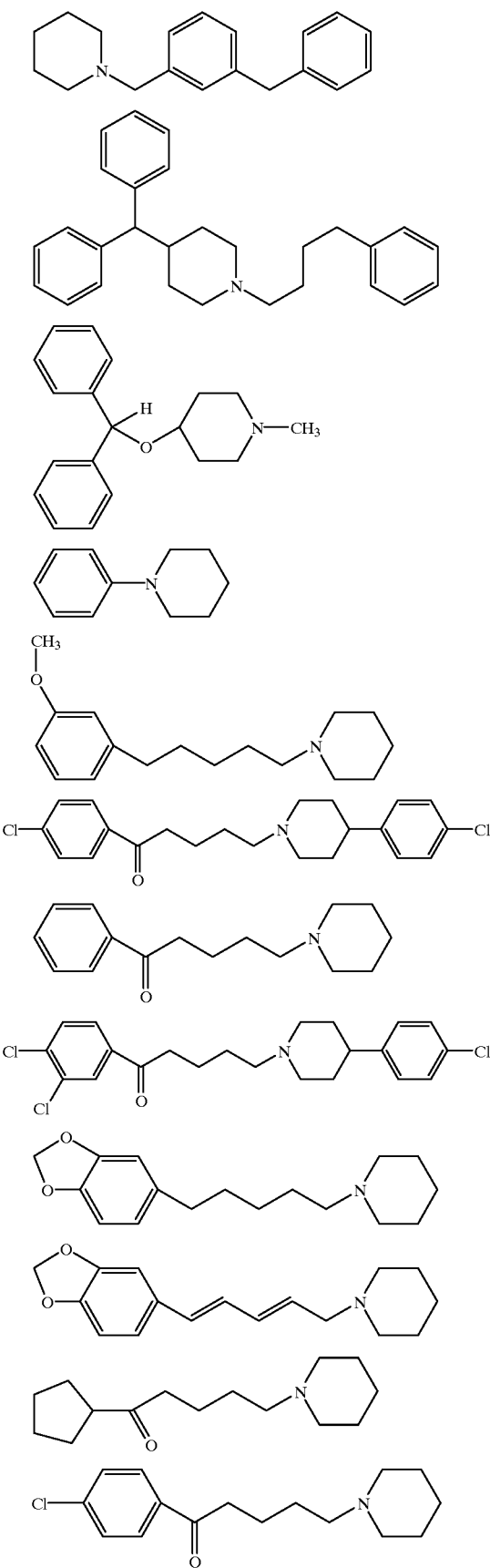
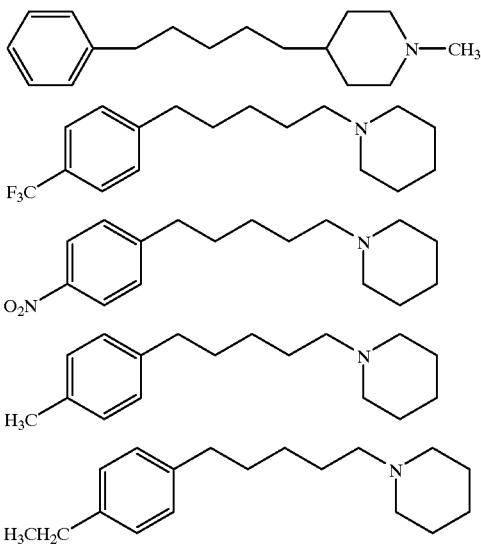

Another aspect of the present invention provides methods of treating a patient in need of such treatment, preferably a mammal, most particularly a human, suffering from a central nervous system disorder, drug abuse, a gastrointestinal disorder, hypertension, migraine, angina and/or depression, which comprises administering to said animal a therapeutically effective amount of one or more compounds of the following Formula II:

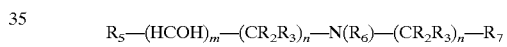

wherein m, n, $R_2$ and $R_3$ are defined as above, $R_6$ is selected from hydrogen and $C_{1-6}$ alkyl; $R_5$ and $R_7$ are each independently selected from the group consisting of; $C_{1-6}$ alkyl, substituted $C_{1-6}$ alkyl, benzyl, substituted benzyl, phenyl, substituted phenyl, benzoyl, substituted benzoyl, wherein the substituents are selected from $C_{1-6}$ alkyl, $C_{1-6}$ alkoxy, halogen, hydroxy, sulfo (—$SO_3H$), trifluoromethyl, etc. In the alternative, $R_1$ may be selected from the following:

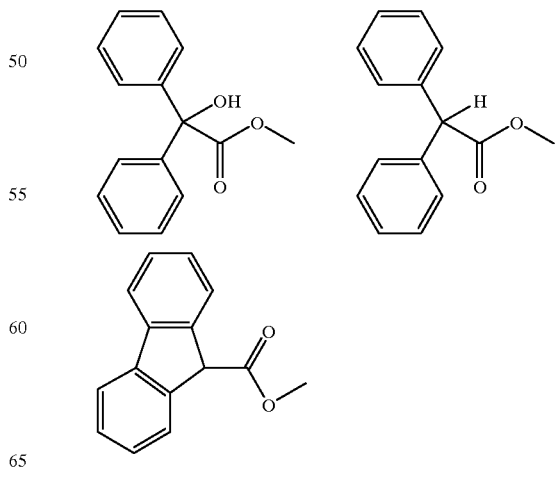

Especially preferred compounds of Formula II include the following structures:

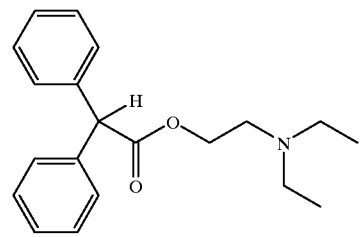

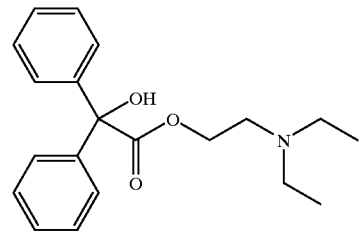

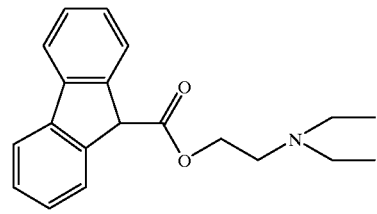

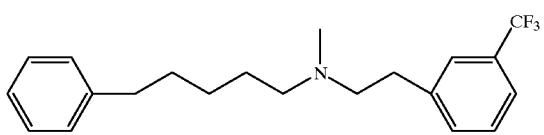

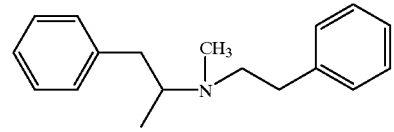

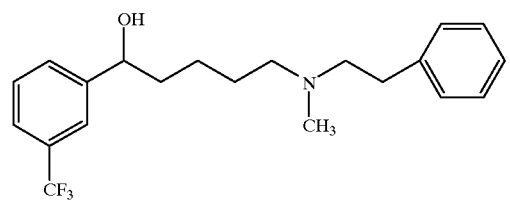

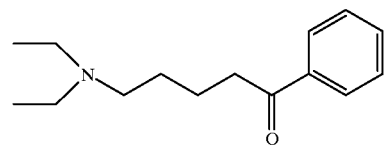

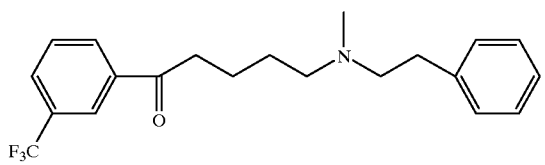

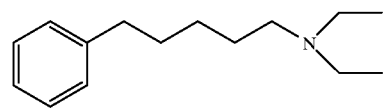

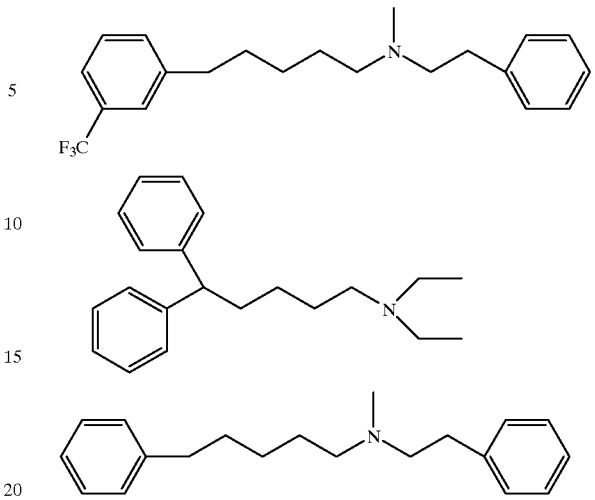

Another aspect of the present invention provides methods of treating an animal, preferably a mammal, particularly a human, suffering from a central nervous system disorder, drug abuse, a gastrointestinal disorder, hypertension, migraine, angina and/or depression, which comprises administering to said animal a therapeutically effective amount of one or more compounds of the following Formula III:

$$R_5-(CR_2R_3)_n-NH-(CR_2R_3)_n-R_6$$

wherein n, $R_2$, $R_3$, $R_5$ and $R_6$ are defined as above.

Especially preferred compounds of Formula III include the following structures:

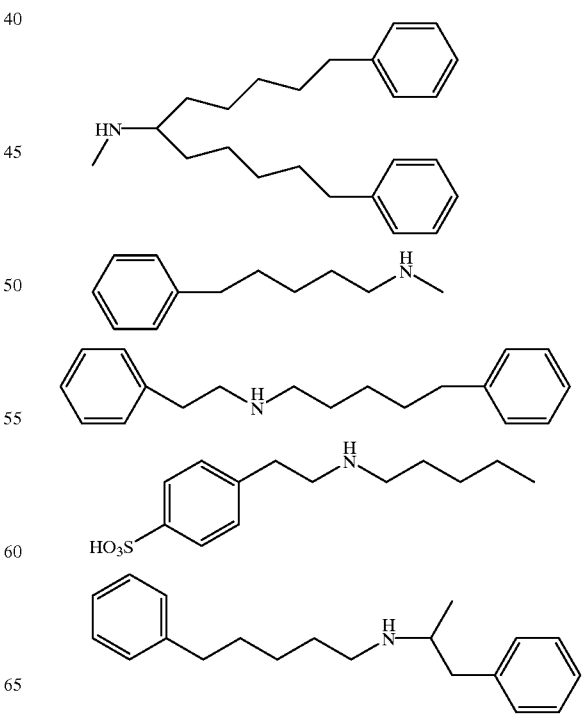

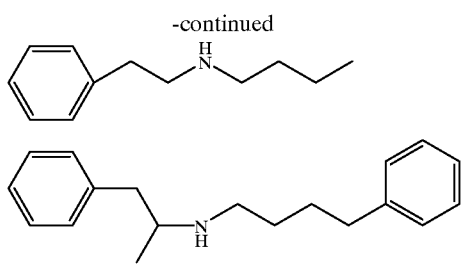

Another aspect of the present invention provides methods of treating an animal, preferably a mammal, particularly a human, suffering from a central nervous system disorder, drug abuse, a gastrointestinal disorder, hypertension, migraine, angina and/or depression, which comprises administering to said animal a therapeutically effective amount of one or more compounds of the following Formula IV:

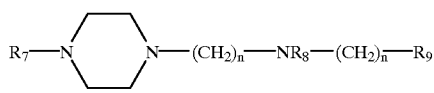

wherein n, m and $R_7$ are each defined as above; $R_8$ is selected from the group consisting of hydrogen, $C_{1-6}$ alkyl, acetyl, etc.; and wherein $R_9$ is selected from the group consisting of; hydrogen, $C_{1-6}$ alkyl, substituted $C_{1-6}$ alkyl, benzyl, substituted benzyl, phenyl, substituted phenyl, benzoyl, substituted benzoyl, wherein the substituents are selected from $C_{1-6}$ alkyl, $C_{1-6}$ alkoxy, halogen, hydroxy, sulfo (—$SO_3H$), trifluoromethyl, etc.

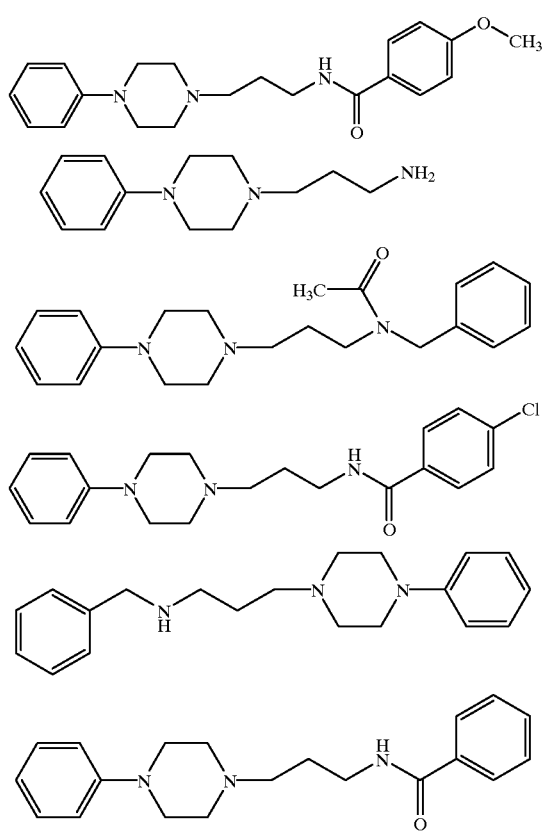

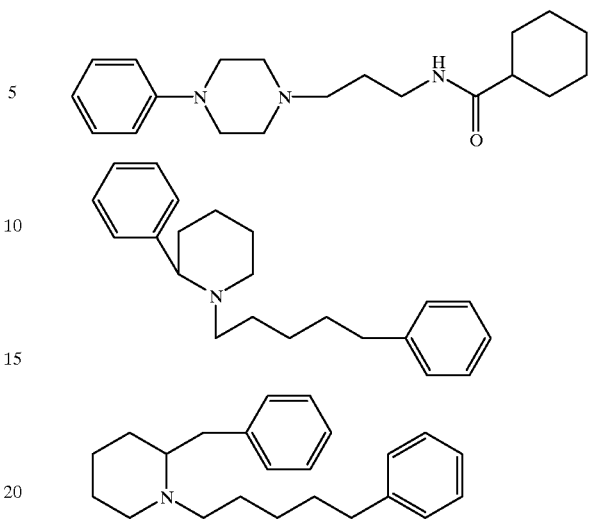

Another aspect of the present invention provides methods of treating an animal, preferably a mammal, particularly a human, suffering from a central nervous system disorder, drug abuse, a gastrointestinal disorder, hypertension, migraine, angina and/or depression, which comprises administering to said animal a therapeutically effective amount of one or more compounds of the following Formula V:

wherein n and m are defined as above; each Ar is independently benzyl, substituted benzyl, phenyl or substituted phenyl (as defined above), and Het is heterocyclic ring having 1 or 2 nitrogen atoms, and from 3 to 8 carbon atoms, as well as from 0 to 3 double bonds, which may likewise be further substituted with $C_{1-6}$ alkyl, $C_{1-6}$ alkylamino, hydroxy, halogen, and other substituents as defined above.

Especially preferred compounds of Formula V include the following structures:

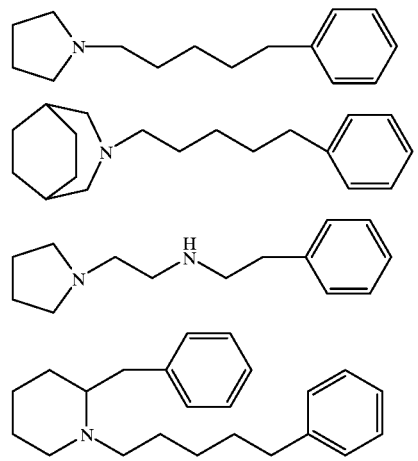

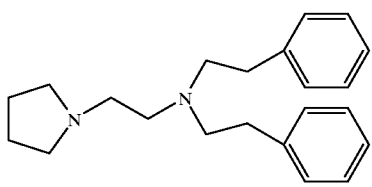

Specifically preferred compounds of Formula VI as defined above include the following:

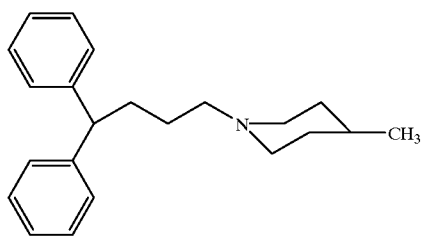

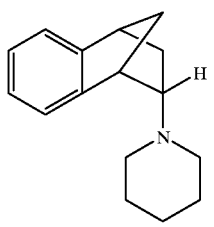

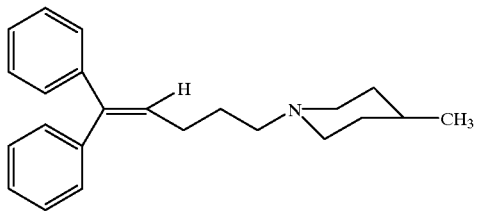

Specifically preferred compounds of Formula VII as defined above include the following:

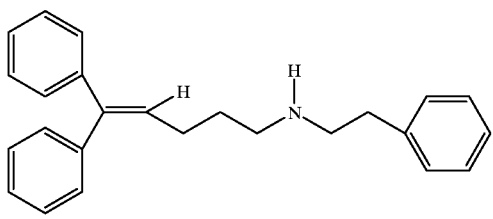

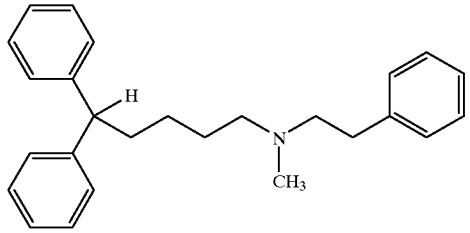

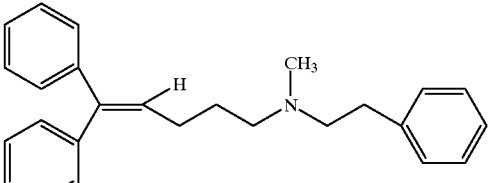

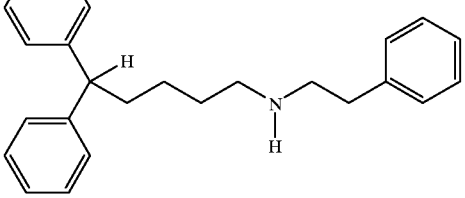

Preferred compounds of the present invention have high binding to the sigma receptors. The sigma receptors include both the sigma-1 and sigma-2 subtypes. See Hellewell, S. B. and Bowen, W. D., *Brain Res.* 527:224–253 (1990); and Wu, X. Z. et al., *J. Pharmacol. Exp. Ther.* 257:351–359 (1991). A sigma receptor binding assay which quantitates the binding affinity of a putative ligand for both sigma sites (against $^3$H-DTG, which labels both sites with about equal affinity) is disclosed by Weber et al., *Proc. Natl. Acad. Sci (USA)* 83:8784–8788 (1986). Alternatively, [$^3$H]pentazocine may be used to selectively label the sigma-1 binding site in a binding assay. A mixture of [$^3$H]DTG and unlabeled (+)pentazocine is used to selectively label the sigma-2 site in a binding assay. The present invention is also directed to certain ligands which are selective for the sigma-i and sigma-2 receptors. See Example 3 which follows. The discovery of such ligands which are selective for one of the two sigma receptor subtypes may be an important factor in identifying compounds which are efficacious in treating central nervous system disorders with minimal side effects.

Suitable halogen substituent groups of compounds of Formulae I–VII (i.e., compounds of the invention) include F, Cl, Br and I. Alkyl groups of compounds of Formulae I–VII preferably have from 1 to about 12 carbon atoms, more preferably 1 to about 8 carbon atoms, still more preferably 1 to about 6 carbon atoms, even more preferably 1, 2, 3 or 4 carbon atoms. Methyl, ethyl and propyl including isopropyl are particularly preferred alkyl groups. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups. Preferred alkenyl and alkynyl groups of compounds of Formulae I–VII have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred. Preferred alkoxy groups of compounds of Formulae I–VII include groups having one or more oxygen linkages and from 1 to about 1 2 carbon atoms, more preferably from 1 to about 8 carbon atoms, and still more preferably 1 to about 6 carbon atoms, even more preferably 1, 2, 3 or 4 carbon atoms. Preferred thioalkyl groups of compounds of Formulae I–VII include those groups having one or more thioether linkages and from 1 to about 12 carbon atoms, more preferably from 1 to about 8 carbon atoms, and still more preferably 1 to about 6 carbon atoms. Thioalkyl groups having 1, 2, 3 or 4 carbon atoms are particularly preferred. Preferred aminoalkyl groups include those groups having one or more primary, secondary and/or tertiary amine groups, and from 1 to about 12 carbon atoms, more preferably one to about 8 carbon atoms, still more preferably 1 to about 6 carbon atoms, even more preferably 1, 2, 3 or 4 carbon atoms. Secondary and tertiary amine groups are generally more preferred than primary amine moieties. Typical heterocyclic groups of a compound of Formulae I–VII contain hetero atoms of N, O and/or S. Suitable heteroaromatic groups of compounds of Formulae I–VII include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzthiazol. Suitable heteroalicyclic groups of compounds of Formulae I–VII include, e.g., tetrahydrofuranyl, tetrahydropyranyl, piperidinyl, morpholino and pyrrolindinyl groups. Suitable carbocyclic aryl groups of compounds of Formulae I–VII include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including 2,5-substituted phenyl and 3-substituted phenyl;

naphthyl including 1-naphthyl and 2-naphthyl; biphenyl; phenanthryl; and anthracyl. Suitable aralkyl groups of compounds of Formulae I–VII include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—CH$_2$-naphthyl).

The substituent groups of the compounds of Formulae I, II, III, IV, V, VI and VII may appear at one or more available positions on the group so substituted. Typical substituent groups used herein include those mentioned above and halogen such as fluoro, chloro, bromo and iodo; cyano; nitro; azido; alkyl groups including those groups having 1 to about 12 carbon atoms or from 1 to about 6 carbon atoms and more preferably 1–4 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; thioalkyl groups including those moieties having one or more thioether linkages and from 1 to about 12 carbon atoms or from 1 to about 6 carbon atoms; and aminoalkyl groups such as groups having one or more N atoms and from 1 to about 12 carbon atoms or from 1 to about 6 carbon atoms.

In regard to the above Formulae I, II, III, IV, V, VI, VII, typical C$_1$–C$_6$ alkyl groups include branched and straight chain groups such as, e.g., methyl, ethyl, n-propyl, i-propyl, n-butyl, t-butyl, i-butyl, pentyl and hexyl groups; typical C$_3$–C$_8$ cycloalkyl groups include cyclopropyl, cyclobutyl, cyclopentyl, cyclohexyl, cycloheptyl, and cyclooctyl groups; typical C$_2$–C$_6$ carboxylic acyl groups include acetyl, propanoyl, i-propanoyl, butanoyl, s-butanoyl, pentanoyl and hexanoyl groups; typical aryl groups include phenyl, naphthyl, phenanthryl, anthracyl and fluorene groups; typical aryl-substituted carboxylic acid groups include the above-mentioned carboxylic acyl groups substituted by one or more aryl groups, e.g., diphenylacetoxy and fluorenecarboxy groups; typical alkaryl groups include the above-listed aryl groups substituted by one or more C$_1$–C$_6$ alkyl groups; typical C$_1$–C$_6$ alkoxycarbonyl groups include carbonyl substituted by methoxy, ethoxy, propanoxy, i-propanoxy, n-butanoxy, t-butanoxy, i-butanoxy, pentanoxy, and hexanoxy groups; typical aralkyl groups include the above-listed C$_1$–C$_6$ alkyl groups substituted by an aryl groups such as those listed above including phenyl, naphthyl, phenanthryl, anthracyl and fluorenyl groups, exemplary aralkyl groups include phenylethyl, phenylpropyl, phenylbutyl, phenylpentyl and phenylhexyl as well as branched chain isomers thereof; typical substituted aralkyl groups include the above-listed aryl groups substituted by one or more halo, hydroxy, C$_1$–C$_6$ alkoxy such as methoxy and alkoxy, amino, and the like, either on the alkyl linkage or the aryl group, or both; typical C$_2$–C$_6$ alkenyl groups include vinyl, allyl, 2-butenyl, 2-pentenyl, and 2-hexenyl groups; typical C$_2$–C$_6$ alkynyl groups include acetynyl and propargyl groups; typical halo groups include fluorine, chlorine, bromine and iodine; typical aroyl groups include carbonyl substituted by phenyl, naphthyl, phenanthryl, and anthracyl groups; typical aralkanoyl groups include carbonyl substituted by the above-listed aralkyl groups; typical aralkoxy groups include the above listed C$_1$–C$_6$ alkoxy groups substituted by phenyl, naphthyl, phenanthryl, and anthracyl groups; typical substituted aryl groups include the above-listed aryl groups substituted by halo, hydroxy, C$_1$–C$_6$ alkoxy, amino, and the like; typical heteroaryl groups include furyl, thienyl, pyrrolyl, thiazolyl, pyridyl, pyrimidinyl, pyrizinyl, oxazolyl and phthalimido groups which may be fused to a benzene ring; typical substituted heteroaryl groups include the above-listed heteroaryl groups substituted by halo, C$_1$–C$_6$ alkyl and the like; typical C$_5$–C$_6$ heterocycloalkyl groups include tetrahydrofuranyl, tetrahydropyranyl, piperidinyl, piperazinyl, morpholino and pyrrolidinyl groups; typical C$_1$–C$_6$ N-alkyl carbamoyl groups aralkyl N-alkyl carbamoyl groups include those groups having carbamoyl moieties substituted by, for example, C$_1$–C$_6$ alkyl (e.g., acetamide) and the above-listed aryl and C$_3$–C$_8$ cycloalkyl groups.

Additional substituent groups for the above include halogen, hydroxy, CF$_3$, C$_1$–C$_6$ acyl, C$_1$–C$_6$ alkyl, C$_2$–C$_6$ alkenyl, C$_2$–C$_6$ alkynyl, C$_1$–C$_6$ alkoxy, C$_6$–C$_{18}$ aryl, C$_2$–C$_6$ dialkoxymethyl, cyano, C$_3$–C$_6$ cycloalkyl, C$_3$–C$_6$ heterocycloalkyl, C$_3$–C$_{15}$ dialkylaminoalkyl, carboxy, C$_2$–C$_6$ carboxylic acid, carboxamido, C$_1$–C$_6$ haloalkyl, C$_1$–C$_6$ haloalkylthio, allyl, C$_7$–C$_{20}$ aralkyl, a C$_3$–C$_6$ heterocycloalkyl ring fused to a benzene ring, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkylamino, C$_2$–C$_{15}$ dialkylamino, hydroxy, carbamoyl, C$_1$–C$_6$ N-alkylcarbamoyl, C$_2$–C$_{15}$ N,N-dialkylcarbamoyl, nitro, C$_2$–C$_{15}$ dialkylsulfamoyl, and the like.

It should be understood that in each of the above Formulae I, II, III, IV, V, VI and VII each substituent is independently selected from the specified groups of substituents. Thus, for example, with respect to Formula VI, each R$_1$, R$_2$ and R$_3$ group can be the same or different and, if n is greater than one, then each R$_2$ substituent is independently selected from the defined group, i.e. each R$_2$ substituent can be the same or different, and each R$_3$ substituent can be the same or different.

Sigma Binding Activities

Under the binding activity studies, an IC$_{50}$ value of at most about 100 nM, preferably at most about 25 nM, more preferably at most 10 nM, most preferably at most 1 nM indicates a high binding affinity with respect to the sigma receptor binding sites. In the present application, the term "high affinity" is intended to mean a compound which exhibits an $IC_{50}$ of less than 100 nM in a sigma receptor binding assay, preferably against $^3$H-DTG as disclosed by Weber et al., *Proc. Natl. Acad. Sci (USA)* 83:8784–8788 (1986), which measures the binding affinity of compounds toward both the sigma-1 and sigma-2 sites. Especially preferred sigma ligands exhibit $IC_{50}$ values of less than about 25 nM, more preferably less than about 10 nM, most preferably less than about 1 nM against $^3$H-DTG.

It has been unexpectedly discovered that certain of the sigma receptor ligands of the present invention exhibit enhanced selectivity to the sigma-1 binding site while other of the sigma receptor ligands exhibit enhanced selectivity to the sigma-2 binding site. Selective binding to the sigma-1 binding site is associated with various gastrointestinal effects, inhibition of contraction of the guinea pig ileum, and inhibition of acetylcholine-induced phosphoinositide response. In contrast, compounds which exhibit selective binding to the sigma-2 receptor may be associated with dystonia and may block calcium channels. See Quiron et al., *Trends Pharm. Sci.*, 13: 85–86 (1992); Rothman et al., *Mol. Pharmacol.*, 39: 222–232 (1991). Thus, the compounds of the present invention which are selective for the sigma-1 receptor may be used for, in addition to the treatment of psychosis, the treatment or prevention of gastrointestinal disorders such as emesis, colitis and the like, without any untoward dystonia. In addition, the compounds of the present invention which are selective for the sigma-2 receptor may be used for treating psychosis and conditions which are ameliorated by calcium channel blockers, e.g. hypertension, migraine and angina. Compounds which are selective for the sigma-2 receptor may be known to produce dystonia. However, antagonists of the sigma-2 receptor are expected to be effective in treating hypertension, migraine and angina without dystonic side effects. Preferably, compounds which are selective for the sigma-1 receptor compared to the sigma-2 receptor have an $IC_{50}$ ratio of sigma-1/sigma-2 of less than about 0.1. See Example 3 which follows.

Surprisingly, the present inventors have also discovered that the sigma receptor ligands of the present invention exhibit low affinity to the DA and PCP receptors. In addition, certain of the sigma receptor ligands of the present invention also exhibit low affinity for the 5-HT$_{IA}$ receptor. Thus, the sigma receptor ligands of the present invention may be used for the treatment of central nervous system disorders without the untoward side effects associated with unwanted binding at the DA, PCP and/or 5-HT$_{1A}$ receptors. By the term "low affinity" is intended a binding affinity of >100 nM, more preferably, >1000 nM in a DA, PCP or 5-HT$_{1A}$ binding assay. Especially preferred sigma receptor ligands have high binding to the sigma receptor and low binding to the DA, PCP and/or 5-HT$_{1A}$ receptors, as defined herein.

The term "central nervous system disorder" as used herein is intended to include both psychiatric and movement dysfunctions. The selective sigma ligands of the present invention may be used to treat psychiatric disorders including psychoses, such as schizophrenia and related disorders, mania with psychotic features, major depression with psychotic features, organic psychotic disorders and other idiopathic psychotic disorders, in addition to anxiety disorders and depression.

The term "schizophrenia" is intended to include any of a group of severe emotional disorders, usually of psychotic proportions, characterized by misinterpretation and retreat from reality, delusions, hallucinations, ambivalence, inappropriate affect, and withdrawn, bizarre, or regressive behavior. See Dorland's *Illustrated Medical Dictionary*, 26th edition, W. B. Saunders Company, Philadelphia, Pa., pp. 1171 (1981). The sigma receptor ligands of the present invention can also be used in treating movement disorders such as Parkinson's disease, tardive dyskinesia, and dystonias. See J. M. Walker et al., *Pharmacol. Rev.*, 42: 355–402 (1990), the disclosure of which is fully incorporated by reference herein.

The sigma receptor ligands of the present invention are also useful for the treatment of drug abuse. In this aspect of the invention, the compounds of the invention are administered to an individual to ameliorate symptoms of drug withdrawal or to reduce craving for the drug, e.g., cocaine, heroin, PCP, hallucinogens such as LSD, and the like.

As discussed above, sigma receptor ligands of the present invention are highly selective for the sigma receptor and show low affinity for the DA and PCP receptors. Certain specific sigma receptor ligands of the present invention also bind with low affinity to 5-HT$_{1A}$ receptors. Thus, in addition to the treatment of central nervous system disorders, the sigma selective ligands of the present invention may also be used as a pharmacological tool in an animal model for the screening of potential sigma receptor agents.

In a further aspect, the invention provides methods for treatment of neurological disorders of a mammal, particularly a human, by administration of a therapeutically effective amount of a compound of the invention (i.e., a compound of Formulae I, II, III, IV, V, VI or VII) to a subject, particularly a human, suffering from or susceptible to a neurological disorder. Exemplary neurological disorders include motor dysfunctions or dystonias such as idiopathic dystonias, neuroleptic-induced dystonias and tardive dyskinesia; disorders associated with seizures or convulsions such as epilepsy; and nervous system dysfunctions resulting from, for example, epilepsy or nerve cell degeneration or nerve cell death. Such nerve cell degeneration or death can result from e.g hypoxia, hypoglycemia, brain or spinal cord ischemia or brain or spinal cord trauma. Typical candidates for treatment for such nerve cell degeneration or death include e.g. heart attack, stroke, patients undergoing surgery where brain or spinal cord ischemia is a potential complication and patients such as divers suffering from decompression sickness due to gas emboli in the blood stream.

Certain evidence indicates that sigma receptors may have a role in the genesis of movement disorders (dystonias) (summarized in J. Walker et al., *Pharmacol. Reviews*, 42(4):355–402 (1990)). For example, there are high concentrations of sigma receptors in various motor-related regions of the brain, such as the cerebellum, red nucleus, ventral spinal cord and part of the substantia nigra (A. Grundlach et al., *J. Neurosci.*, 6:1757–1770 (1986); A. Graybiel et al., *J. Neurosci.*, 9:326–338 (1989)). Further, it has been found that the injection of small amount of sigma ligands into such motor areas can cause pronounced effects on motor behavior, such as a torticollis-like dystonia, vigorous circling behavior or vacuous chewing movements (J. Walker et al., *Neurology*, 38:961–965 (1988); S. Patrick et al., *Eur. J. Pharmacol.*, 231:243–249 (1993)). These motor behaviors show distinct similarities to certain human motor dysfunctions such as idiopathic dystonias, neuroleptic-induced dystonias and tardive dyskinesia (J. Walker, *Pharmacol. Reviews*, 42(4):355–402 (1990)). Direct effects of the sigma ligands in these brain regions have been shown on physiological or biochemical parameters (R. Matsumoto et al., *Eur. J. Pharmacol.*, 158:161–165 (1988); S. Patrick et al., Eur. J. Pharmacol., 231:243–249 (1993)). The testing of a number of drugs and correlations with their sigma-receptor affinities suggests that these are sigma receptor-mediated effects, and more specifically, may involved the sigma-2 receptor subtype (R. Matsumoto et al., Pharmacol., Biochem. and Behavior, 36(1):151–155 (1990); J. Walker et al., Eur. J. Pharmacol., 231:61–68 (1993)). Therefore it appears that sigma receptors are important in the motor behaviors produced or mediated by these brain regions, and that the proper pharmacological manipulation of these receptors could have beneficial effects in a number of motor dysfunctions or dystonias. Several studies have shown anticonvulsant activities for a number of sigma ligands. For instance, Roth et al. showed that di-2-tolyl-guanidine (DTG) is anticonvulsant in rat cortex (J. Roth et al., Eur. J. Pharmacol., 236(2):327–331 (1993)). Also, Ritz and George found cocaine-induced seizures to be inhibited by drugs acting at sigma receptors (M. Ritz et al., FASEB J., J4(3):A745 (1990)), and Kadaba has described a class of compounds which act as sigma selective anticonvulsants (P. Kadaba, Abstr. Am. Chem. Soc., 204(1–2):medi73 (1992)).

The protection of nervous tissue against various types of insult, particularly ischemia such as results from stroke or head trauma, has been a fruitful area of recent research, and has led to an improved understanding of the biochemical processes which mediate ischemic damage. In particular, knowledge of the excessive glutamate release in ischemic brain and the actions of glutamate on its neuronal receptors has supported the excitotoxic theory of such neuronal damage, and led to a variety of models for the testing of drugs for neuroprotective activity. Importantly, certain sigma ligands have been found to be neuroprotective in such models. The compound opipramol, a potent sigma receptor ligand, was found in vivo to protect against ischemia in gerbils and also to have biochemical effects consistent with modulation of the NMDA-type of glutamate receptors; similar biochemical effects were found with a number of other sigma ligands (T. Rao et al., Neuropharmacol., 29(12):1199–1204 (1990); T. Rao et al., Brain Res., 561:43–50 (1991)). In addition, several sigma ligands, including BMY-14802 caramiphen and haloperidol, were found to have in vivo protective effects against NMDA-induced toxicity and seizures (M. Pontecorvo et al., Brain Res. Bull., 26:461–465 (1991)), and several sigma ligands were found to inhibit ischemia-induced glutamate release from hippocampal slice preparations in vitro (D. Lobner et al., Neuroscience Lett., 117:169–174 (1990)). Thus certain compounds that exhibit affinity to the sigma receptor also exhibit actions indicative of neuroprotection in several models relevant to brain ischemia.

The sigma receptor ligands of the present invention may also be radiolabelled with, for example, $^3H$, $^{11}C$, $^{14}C$, $^{16}F$, $^{125}I$, $^{131}I$, and the like.

In their radiolabelled form, the sigma receptor ligands of the present invention may be used for autoradiography studies of the sigma receptor sites in tissue, especially neuronal tissue.

The sigma receptor ligands of the present invention may be prepared by methods of synthesis as disclosed in Example 1 herein and in PCT Application WO 93/00313, incorporated herein by reference for its disclosure of synthesis and use of sigma receptor ligands. The starting materials for the compounds of the present invention may likewise be prepared by general methods of organic synthesis.

For general methods of preparing such compounds, reference is made to Fuller, R. W. et al., J. Med. Chem., 14: 322–325 (1971); Foye, W. O. et al., J. Pharm. Sci., 68: 591–595 (1979); Bossier, J. R. et al., Chem. Abstr., 66: 46195h and 67: 21527a (1967); Aldous, F. A. B., J. Med. Chem., 17: 1100–1111 (1974); Fuller, R. W. et al., J. Pharm. Pharmacol., 25: 828–829 (1973); Fuller, R. W. et al., Neuropharmacology, 14: 739–746 (1975); Conde, S. et al., J. Med. Chem., 21: 978–981 (1978); Lukovits, I. et al., Int. J. Quantum Chem., 20: 429–438 (1981); and Law, B., J. Chromatog., 407: 1–18 (1987), the disclosures of which are incorporated by reference herein in their entirety. Radiolabelled derivatives may be prepared by, for example, using a tritiated reducing agent to perform the reductive amination or by utilizing a $^{14}C$-labelled starting material. Alternatively, N-substituted carboxamide starting materials may be reduced, for example, with $LiAlH_4$ to give the N,N-disubstituted sigma receptor ligand. Similarly, where the starting compound comprises a carbonyl group, such a compound may be reduced with, for example, $AlH_3$, diborane:methyl sulfide or other standard carbonyl reducing reagent to give the sigma receptor.

Also included within the scope of the present invention are the optical isomers of the compounds of the invention. The optical isomers may be separated by classical resolution techniques by, for example, formation of a salt of the amino group with an optically active acid. A particularly preferred acid for this purpose is (+)-di-p-toluoyl-D-tartaric acid. The resulting diastereoisomeric salt may then be separated by crystallization, chromatography, or by taking advantage of the differing solubilities of the two diastereoisomeric salts. The free base may then be isolated by treatment with a base such as aqueous ammonia and extraction with an organic solvent. Alternatively, the optical isomers may be prepared by resolution of the starting amine used to prepare the optically active compound of the invention.

The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic, and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic anion exchange resins, such as isopropylamine, trimethylamine, diethylamine, triethylamine, tripropylamine, ethanolamine, 2-dimethylaminoethanol, 2-2 -diethylaminoethanol, tromethamine, lysine, arginine, histidine, caffeine, procaine, hydrabamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

Especially preferred pharmaceutically acceptable salts of the compounds of the invention include acid addition salts. Acid addition salts are formed by mixing a solution of the sigma ligand of the invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like.

In the methods of treatment of the present invention, the pharmaceutical compositions may comprise the sigma receptor ligand at a unit dose level of about 0.01 to about 500 mg/kg, preferably from about 0.05 to about 50 mg/kg, most preferably from about 0.2 to about 5 mg/kg of body weight of the recipient (or patient), which preferably is mammal, particularly a human, or an equivalent amount of the pharmaceutically acceptable salt thereof, on a regimen of 1–4 times per day. Of course, it is understood that the exact treatment level will depend upon the case history of the recipient that is treated. The precise treatment level can be determined by one of ordinary skill in the pharmaceutical or compounding arts without resort to undue experimentation.

For example, therapeutically effective amounts of compounds) of the invention can vary with factors such as a patient's weight, age and general health, the efficacy of the particular compound and formulation, route of administration, nature and extent of the condition being treated, and the effect desired.

The pharmaceutical compositions of the invention may be administered to any recipient (animal or human) which may experience the beneficial effects of the compounds of the invention. Foremost among such recipients are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. As discussed above, the dosage administered will be dependent upon the age, health, and weight of the recipient, kind of concurrent treatment, if any, frequency of treatment, and the nature of the effect desired.

In addition to the sigma receptor ligands, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragées, and capsules, and also preparations which can be administered rectally, such as suppositories, as well as suitable solutions for administration by injection or orally, are present at a concentration of from about 0.01 to 99 percent, together with the excipient.

The pharmaceutical preparations of the present invention are manufactured in a manner which is itself known, for example, by means of conventional mixing, granulating, dragée-making, dissolving, or lyophilizing processes. Thus, pharmaceutical preparations for oral use can be obtained by combining the sigma ligand with solid excipients, optionally grinding the resulting mixture and processing the mixture of granules, after adding suitable auxiliaries, if desired or necessary, to obtain tablets or dragée cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol.

Dragée cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragée coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol.

The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the sigma ligands in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

All documents cited herein are incorporated herein by reference.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius. These examples are illustrative of the method and compositions of the present invention. Other suitable modifications and adaptations of the sigma receptor ligands as well as the variety of conditions and parameters normally encountered in clinical therapy and which will be apparent to those skilled in the art are within the spirit and scope of the invention.

General Comments

In the following Examples, proton ($^1$H) magnetic resonance spectra were obtained on JEOL FX90X or QE 300 (300 MHz) spectrometers with tetramethyl-silane (TMS) as internal standard. Melting points were determined on a Thomas Hoover apparatus and are uncorrected. Elemental analysis was performed by Atlantic Microlab and determined values are within 0.4% of calculated values.

Phenylpiperidines used in the syntheses were obtained either commercially or by hydrogenation of the commercially available tetrahydropyridines. Hydrogenation of tetrahydropyridines was typically conducted as disclosed below for preparation of 4-(4-fluorophenyl)piperidine from 4-(4-fluorophenyl)-1,2,3,6-tetrahydropyridine. Intermediates for the preparation of selected compounds were obtained by Grignard reaction or Friedel-Crafts selective acylation. For example, 5-chlorovaleronitrile and an appropriately substituted magnesium bromide were allowed to react to obtain the desired phenyl-5-chloropentanones, and 1-(4-methoxyphenyl)-5-chloropentanone was prepared by reacting 5-chlorovaleryl chloride with anisole. Phenylpentyl bromide was prepared by a conventional method.

4-(4-Fluorophenyl)piperidine used to prepare compounds of the invention was synthesized as follows. A mixture of 4-(4-fluorophenyl)-1,2,3,6-tetrahydropyridine (2.2 9, 10 mmol), 10% Pd/C (0.4 g) and glacial HOAc (50 mL) was hydrogenated at 50 psi in a Paar® hydrogenator overnight (~18 h). The catalyst was removed by filtration, washed with MeOH (60 mL), and the combined filtrate and washings were evaporated under reduced pressure. Water (20 mL) was added to the residue, followed by solid NaOH, until the solution was basic. The resulting solution was extracted with Et$_2$O (2×30 mL). The combined Et$_2$O extract was washed with H$_2$O (10 mL), dried (MgSO$_4$), and the solvent was removed in vacuo to afford an oil. $^1$H-NMR analysis of the oil showed the absence of olefinic protons; the oil was used without further purification or characterization.

EXAMPLE 1

Synthesis of Compounds of the Invention

Compounds of the invention can be prepared according to the following Methods A–C.

Method A 1,2,4-Dichlorophenyl-5-[4-(4-chlorophenyl)-1-piperidino]pentanone Hydrochloride (Compound 1). A solution of 1-bromo-3,4-dichlorobenzene (8 g, 35 mmol) in anhydrous Et$_2$O (50 mL) was added to a mixture of magnesium (0.85 g, 35 mmol) and anhydrous Et$_2$O (100 mL) in a portionwise manner under N$_2$. After about 5 mL of the solution was added, the reaction mixture was allowed to stir until reaction has commenced. The remainder of the solution was added to allow gentle reflux and the reaction mixture was heated under reflux for additional 1 h. A solution of 5-chlorovaleronitrile (3.5 g, 30 mmol) in anhydrous Et$_2$O (50 ml), was added to the Grignard solution over 5 minutes, and refluxing was continued for 1.5 hours. The reaction mixture was poured into an ice-water mixture (300 g) and concentrated H$_2$SO$_4$ (50 mL) was cautiously added. The resulting mixture was extracted with Et$_2$O (3×50 mL), washed with 10% Na$_2$CO$_3$ (20 mL), then H$_2$O (20 mL) and dried (MgSO$_4$). The solvent was removed under reduced pressure and the residue chromatographed over silica gel (30 g) and eluted with hexane followed by 10% hexane in EtOAc. The desired product was obtained as a yellowish oil (2.2 g, 28%).

A stirred mixture of 4-(3,4-dichlorophenyl)-5-chloropentanone (0.8 g, 3.0 mmol), 4-(4-chlorophenyl)piperidine (0.5 g, 2.5 mmol), KI (20 mg), and K$_2$CO$_3$ (0.8 g, 5.8 mmol) in 1,2-dimethoxyethane (DME) (6 mL) was heated under reflux for 20 hours and allowed to cool to room temperature. The mixture was partitioned between Et$_2$O (30 mL) and 10% NaOH (15 mL). The aqueous portion was extracted twice with (30 mL); the Et$_2$O solutions were combined, washed with H$_2$O (10 mL), and dried (MgSO$_4$). Solvent was removed under reduced pressure. The residue was converted to the HCl salt and recrystallized from MeOH/anhydrous Et$_2$O to provide the title compound (620 mg, 56%); mp 187–188° C.

Method B 1-(4-Methoxyphenyl)-5-(4-phenyl-1-piperidino) pentanone Hydrochloride (Compound 2). A solution of chlorovaleryl chloride (6.0 g, 39 mmol) was added in a dropwise manner to a stirred mixture of anisole (4.5 g, 42 mmol) and anhydrous AlCl$_3$ (14.0 g) in CH$_2$Cl$_2$ (100 mL) under N$_2$ at 0° C. Stirring was continued at 0° C. for 1 hour; the ice-bath was removed and the mixture was allowed to stir at room temperature for 2 hours. The reaction mixture was poured into an ice-water mixture (300 g) and the organic layer was separated. The CH$_2$Cl$_2$ solution was washed with 5% NaOH (20 mL), H$_2$O (20 mL), and then dried (MgSO$_4$). The solvent was removed under reduced pressure and the resulting oil formed crystals on standing. The crystals were washed with petroleum ether (bp 40–60° C.) to afford the desired product (3.3 g, 38%); mp 67–70° C.

A stirred mixture of 4-phenylpiperidine (0.34 g, 2.1 mmol), 1-(4-methoxyphenyl)-5-chloropentanone (0.5 g, 2.2 mmol), KI (10 mg, and K$_2$CO$_3$ (0.4 g, 2.9 mmol) in DME (3 mL) was heated under reflux for 22 hours and allowed to cool to room temperature. The mixture was partitioned between Et$_2$O (3×30 mL) and 10% NaOH (15 mL). The Et$_2$O portions were combined, washed with H$_2$0 (15 mL), and dried (MgSO$_4$). Solvent was removed under reduced pressure and the residue was converted to the HCl salt. The salt was recrystallized from MeOH/anhydrous Et$_2$O to afford white crystals of the title compound (0.62 g, 76%); mp 216–218° C.

Method C

N-[5-(4-Chlorophenyl)pentyl]piperidine Hydrochloride (Compound C). Triethylsilane (0.4 g, 4.3 mmol) was added to an ice-cold and stirred solution of 1-(4-chlorophenyl)-5-(1-piperidino)pentanone (0.2 g, 0.6 mmol) in trifluoroacetic acid (TFA) (1.1 g, 9.5 mmol). The mixture was allowed to stir at room temperature for 48 hours, hexane (10 mL) was added, and stirring was continued for 30 minutes. The TFA solution was basified with 10% NaOH, then extracted with Et$_2$O (3×25 mL) and dried (MgSO$_4$). The HCl salt was prepared and recrystallized from a mixture of methyl ethyl ketone (MEK)/MeOH/Et$_2$O to provide the title compound (41 mg, 21%); mp 149–151° C. Analyzed for C, H, N; H calc.=8.43%, found=7.94%.

By using the above Methods A–C and/or modifications thereof as specified in the following Table 1, Compound Nos. 4–25 of the following formula were prepared:

TABLE I

X—⟨phenyl⟩—Z—CH₂CH₂CH₂CH₂—N⟨piperidine⟩(W)(Y)

| Cmpd. No. | X | Z | db[a] | Y | W | Method | mp °C. | Yield % | RS[b] | Formula |
|---|---|---|---|---|---|---|---|---|---|---|
| 4 | 4-F | C=O | − | 4-Cl-phenyl | OH | A | 192–194 | 16 | Et₂O/MeOH | $C_{22}H_{25}NClFO_2 \cdot HCl$ |
| 5 | 4-F | C=O | − | phenyl | H | A | 197–199 | 52 | EtoAc | $C_{22}H_{26}NFO \cdot HCl$ |
| 6 | H | C=O | − | phenyl | H | A | 192–194 | 44 | Et₂O/MeOH | $C_{22}H_{27}NO \cdot HCl$[c] |
| 7 | 4-Cl | C=O | − | phenyl | H | A | 210–211 | 27 | EtoAc/MeOH | $C_{22}H_{26}NClO \cdot HCl$ |
| 8 | 3-Cl | C=O | − | phenyl | H | A | 170–172 | 19 | MEK | $C_{22}H_{26}NClO \cdot HCl$ |
| 9 | 3-OCH₃ | C=O | − | phenyl | H | A | 158–159 | 21 | MEK | $C_{23}H_{29}NO_2 \cdot HCl$ |
| 10 | 4-Cl | C=O | − | 4-Cl-phenyl | H | A | 168–170 | 25 | MeOH | $C_{22}H_{25}NCl_2O \cdot C_2H_2O_4$ |
| 11 | 4-Cl | C=O | − | 4-F-phenyl | H | A | 197–199 | 52 | EtoAc | $C_{22}H_{26}NFO \cdot HCl$ |
| 12 | 4-Cl | C=O | + | 4-Cl-phenyl | H | A | 203–205 | 25 | Et₂O/MeOH | $C_{22}H_{23}NCl_2O \cdot HCl$ |
| 13 | 4-Cl | C=O | + | 4-F-phenyl | H | A | 213–215 | 20 | Et₂O/MeOH | $C_{22}H_{23}NClFO \cdot HCl$[c] |
| 14 | H | CH₂ | − | phenyl | H | A | | | | |
| 15 | 4-Cl | CH₂ | − | phenyl | H | A | | | | |
| 16 | 4-OCH₃ | CH₂ | − | phenyl | H | A | | | | |
| 17 | H | C=O | − | H | H | A | 158–160 | 22 | EtOH | $C_{16}H_{23}NO \cdot C_2H_2O_4$ |
| 18 | 4-F | C=O | − | H | H | A | 158–160 | 23 | MeOH | $C_{16}H_{22}NFO \cdot C_2H_2O_4$ |
| 19 | 4-Cl | C=O | − | H | H | A | 173–175 | 30 | CH₂Cl₂/MeOH | $C_{16}H_{22}NClO \cdot HCl$ |
| 20 | 3-Cl | C=O | − | H | H | A | 155–157 | 16 | MeOH | $C_{16}H_{22}NClO \cdot C_2H_2O_4$[c] |
| 21 | 4-OCH₃ | C=O | − | H | H | A | 174–175 | 35 | Et₂O/EtOH | $C_{17}H_{25}NO_2 \cdot HCl$ |
| 22 | 3-OCH₃ | C=O | − | H | H | A | 158–160 | 34 | EtOH | $C_{17}H_{25}NO_2 \cdot C_2H_2O_4$ |
| 23 | H | CH₂ | − | H | H | | | | | |
| 24 | 4-OCH₃ | CH₂ | − | H | H | C | 131–133 | 100 | EtOAc/MeOH | $C_{17}H_{27}NO \cdot HCl$ |
| 25 | 3-OCH₃ | CH₂ | − | H | H | C | 95–96 | 50 | MEK | $C_{17}H_{27}NO \cdot C_2H_2O_4$ |

[a]Presence (+) or absence (−) of a $C_3$–$C_4$ double bond in the piperidine ring.
[b]RS = Recrystallization solvent
[c]Crystallized with 0.25 moles $H_2O$ EXAMPLE 2
Sigma Receptor Binding Assay Sigma receptor binding assays using guinea pig brain membrane homogenates and the radioligand [³H]DTG were conducted as described by Weber et al., P.N.A.S. (USA), 83: 8784–8788 (1986) which indicates binding to both the sigma-1 and sigma-2 sites. Briefly, frozen whole guinea-pig brains (Biotrol, Indianapolis, Ind.) were homogenized in 10 volumes (w/v) of ice-cold 320 mM sucrose using a Brinkman® polytron. The homogenate was centrifuged at 1,000× g for 20 minutes at 4° C. The supernatant was centrifuged at 20,000× g for 20 minutes at 4° C. The resulting pellet was resuspended in 10 initial volumes of 50 mM Tris/HCl buffer at pH 7.4 and centrifuged at 20,000× g for 20 minutes at 4° C. The resulting pellet was resuspended in 5 initial volumes ice-cold 50 mM Tris/HCl (pH 7.4), and the final volume was adjusted to yield a protein concentration of 3 mg/mL. Aliquots of 20 mL were stored at −70° C. until used, with no detectable loss of binding.

For [³H]DTG binding assays, the frozen membrane suspensions were thawed and diluted 1:3 in 50 mM Tris/HCl (pH 7.4). To 12×75 mm polystyrene or glass test tubes were added 0.8 ml of diluted membrane suspension, 0.1 ml of [³H]DTG (Dupont/NEN) to yield a final concentration of 1.4 nM, and 0.1 ml of unlabelled drugs or buffer. The protein concentration in the 1-ml final incubation volume was 800 μg/ml, corresponding to 32 mg of brain tissue (original wet weight) and to a tissue concentration within the linear range for specific binding.

The volume of the assays may be changed, specifically halved, so long as the concentrations of the constituents remain the same. Non-specific binding was defined as that remaining in the presence of 10 μM haloperidol. Incubations were terminated after 90 minutes at room temperature by addition of 4 ml of ice-cold 50 mM Tris/HCl (pH 7.4) and rapid filtration of the membrane suspension through Whatman® GF/B or Schleicher & Schuell #32 glass-fiber filters under vacuum, using a 48-well cell harvester (Brandel). The filters were washed 2 times with 4 mL of 50 mM Tris/HCl (pH 7.4). Each filter was suspended in 10 ml Cytoscint (ICI), and radioactivity was measured by liquid scintillation spectrometry at a counting efficiency of approximately 50%. $IC_{50}$ values (indicated as $K_i$ in Tables II below) were determined by non-linear regression analysis. Compound numbers identified in Table II indicate the compound identified by the same compound number in Example 1 above.

TABLE II

| Compound No. | Ki nM | (± SEM) |
|---|---|---|
| 1 | 1.8 | (0.1) |
| 2 | 0.8 | (0.05) |
| 3 | 2.0 | (0.5) |
| 4 | 2.6 | (0.3) |
| 5 | 0.8 | (0.1) |
| 6 | 0.9 | (0.02) |
| 7 | 0.5 | (0.1) |
| 8 | 1.1 | (0.2) |
| 9 | 1.0 | (0.3) |
| 10 | 1.8 | (0.1) |
| 11 | 1.0 | (0.1) |
| 12 | 4.3 | (0.1) |
| 13 | 2.0 | (0.6) |
| 14 | 0.9 | (0.2) |
| 15 | 1.8 | (0.5) |
| 16 | 1.2 | (0.04) |
| 17 | 25.2 | (4.2) |
| 18 | 6.7 | (1.4) |
| 19 | 1.2 | (0.3) |
| 20 | 3.8 | (0.5) |
| 21 | 9.9 | (1.5) |
| 22 | 20.7 | (2.1) |
| 23 | 1.9 | (0.2) |
| 24 | 4.7 | (0.9) |
| 25 | 10.7 | (2.9) |

EXAMPLE 3

Sigma-1 and Sigma-2 Binding Assay Methods

Compounds of the inventions were tested for selective binding to the sigma-1 receptor and sigma-2 receptor with results set forth in columns in the tables which follow. The structures of the tested compounds are shown in the tables. The tested compounds were prepared in accordance with the methods disclosed herein and as known in the art. Several compounds were also tested by the assay of Example 2, and the results thereof are shown in the first table which follows under the column of "SIGMA $IC_{50}$". Protocols of the Sigma-1 and Sigma-2 binding assays employed are as follows:

Sigma-1 binding assay ($[^3H](+)$pentazocine)

The sigma-1 selective binding assay was performed using $[^3H](+)$pentazocine as the radioligand (3–4 nM final concentration unless otherwise specified) and approximately 100 pg of guinea pig brain membranes in a final volume of 500 µl of 50 mM TRIS-HCl, pH 8.0. Non-specific binding was determined in the presence of 10 µM haloperiodol. For the standard equilibrium assay the mixtures were incubated for 4–5 hours at 37° C., quenched with 4 ml of ice cold incubation buffer and rapidly filtered over Whatman GF/B glass fiber filters, followed by three 4 ml rinses with additional ice cole incubation buffer. The radioactivity on the filters was determined as described in Example 2 above.

Sigma-2 binding assay

The Sigma-2 selective binding assay was performed using about 2 nM $[^3H]$DTG as the radioligand in the presence of 200 nM (+)pentazocine to block the Sigma-1 sites, with 400 µg of guinea pig brain membranes in a total volume of 0.5 ml of 50 mM TRIS-HCl, pH 7.4. Non-specific binding was determined in the presence of 10 µM haloperidol. For the standard equilibrium assay the mixtures were incubated for 30 minutes at room temperature, then filtered and the radioactivity determined as described for the standard $[^3H]$DTG assay as described above in Example 2.

| Structure | SIGMA IC50 (nM) | Sigma 1 Ki (nM) | Sigma 2 IC50 (nM) |
|---|---|---|---|
| (methylenedioxyphenyl-butyl-piperidine) | 2.25 | | |
| (phenyl-butyl-N-methyl-phenethylamine) | 1.3 | 0.25 | 4.98 |
| (bis(phenylbutyl)-N-methylamine) | 2.97 | | |
| (phenyl-butyl-NH-phenethylamine) | 3.66 | | |
| (phenyl-butyl-pyrrolidine) | 4.95 | 0.76 | 69.7 |
| (3-CF3-phenyl-butyl-N-methyl-phenethylamine) | | 0.59 | 3.57 |
| (phenyl-butyl-N-methyl-(3-CF3-phenethyl)amine) | | 1.74 | 14.4 |

-continued

| Structure | Sigma 1 Ki (nM) | Sigma 2 IC50 (nM) |
|---|---|---|
| 3-(trifluoromethyl)phenyl ketone with N-methyl-N-phenethylaminopentyl chain | 0.71 | 1.27 |
| 1-(3-(trifluoromethyl)phenyl)-1-hydroxy with N-methyl-N-phenethylaminobutyl chain | 0.95 | 3.02 |
| 4-benzyl-1-(3-phenylpropyl)piperidine | 0.75 | 3.14 |
| 1-benzyl-4-(3-phenylpropyl)piperidine | 0.2 | 9.39 |

| Structure | Sigma 1 Ki (nM) | Sigma 2 IC50 (nM) |
|---|---|---|
| 1-methyl-4-(5-phenylpentyl)piperazine | 1.44 | 78.9 |
| 1-methyl-4-(5-phenylpentyl)piperidine | 0.6 | 97.3 |
| 1-(5-(benzo[d][1,3]dioxol-5-yl)pentyl)piperidine · C₂H₂O₄ | 0.32 | 63.4 |
| 1-(5-(4-nitrophenyl)pentyl)piperidine · C₂H₂O₄ | 0.16 | 9.91 |
| 2-piperidinyl-benzonorbornane · HBr | 0.13 | 5.29 |
| 3-phenyl-1-(4-phenylbutyl)piperidine · C₂H₂O₄ | 0.07 | 4.17 |

-continued
| Structure | | |
|---|---|---|
| 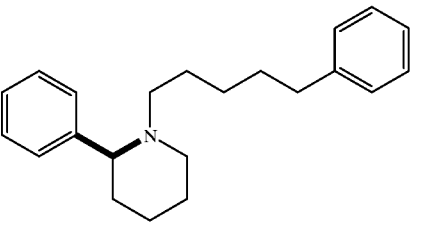 | 0.16 | 4.7 |
| 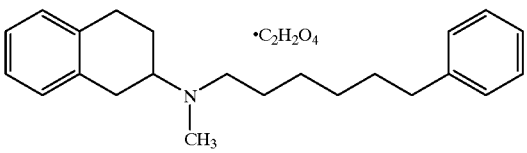 | 0.61 | 170 |
| 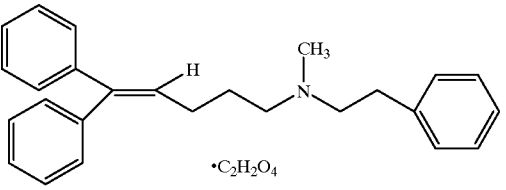 | 0.90 | 40.8 |
| 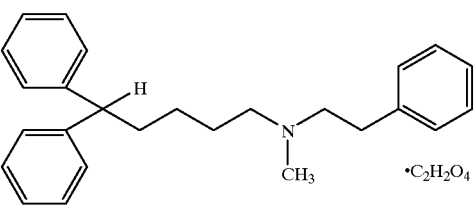 | 0.48 | 31.5 |
| 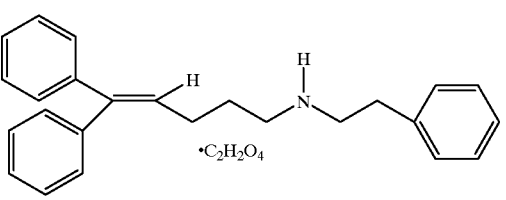 | 1.3 | 142 |
| 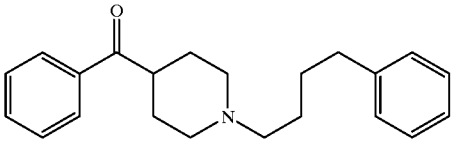 | 3.99 | 10.8 |
| 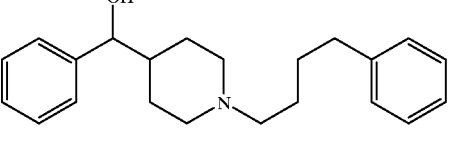 | 1.72 | 12.54 |
| 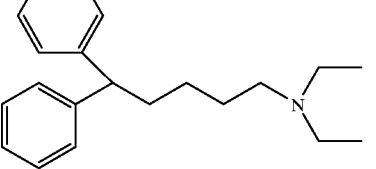 | 1.42 | 51.23 |

-continued
| | | |
|---|---|---|
| 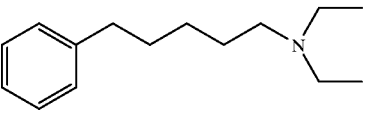 | 6.01 | 88.53 |
| 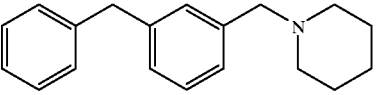 | 5.44 | 98.17 |
| 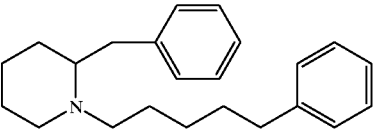 | 0.36 | 10.43 |
| 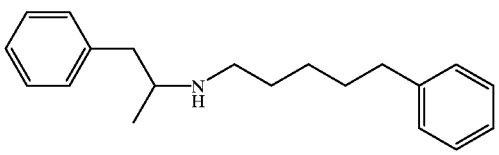 | 0.54 | 10.89 |
| 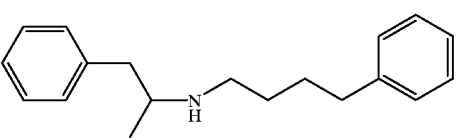 | 7.38 | 47.47 |
| 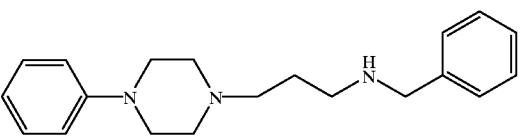 | 1.96 | 101.3 |
| 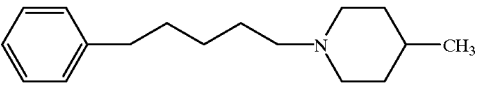 | 0.08 | 7.1 |
| 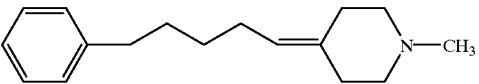 | 9.87 | 257.5 |
| 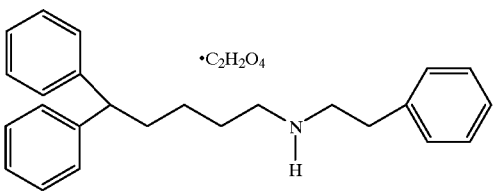 | 0.68 | 100 |

-continued

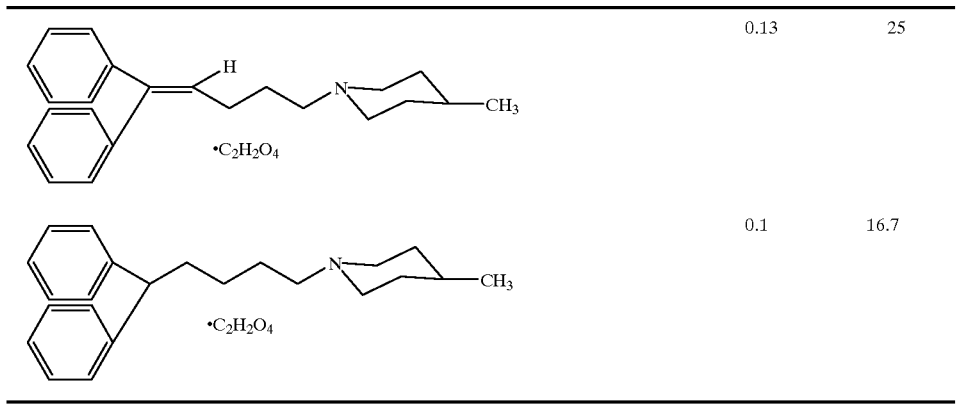

What is claimed is:

1. A method of treating a human being suffering from, drug abuse, gastrointestinal disorder, hypertension, migraine, angina or depression which comprises administering to said human a therapeutically effective amount of a compound of Formula I:

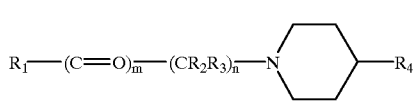
(I)

wherein m is 0 or 1; n is 0, 1, 2, 3, 4, 5, or 6; $R_1$ is selected from $C_{1-6}$ alkyl, $C_{3-6}$ cycloalkyl, phenyl, substituted phenyl, naphthyl, substituted naphthyl, indane, substituted indane, tetralin, substituted tetralin, benzocycloheptane, substituted benzocycloheptane, wherein the substituents are selected from $C_{1-6}$ alkyl, $C_{1-6}$ alkoxy, halogen, hydroxy, $C_{1-6}$ alkyl, trifluoromethyl;

or wherein $R_1$ is:

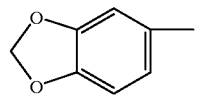

$R_2$ and $R_3$ are each independently selected from hydrogen, hydroxy, $C_{1-6}$ alkyl, or together two $R_2$ and $R_3$ groups may be a double bond between adjacent carbon atoms; $R_4$ is hydrogen, $C_{1-6}$ alkyl, substituted $C_{1-6}$ alkyl, benzyl, $C_{2-6}$ alkaryl, benzoyl, phenyl, substituted phenyl, naphthyl, substituted naphthyl, indane, substituted indane, tetralin, substituted tetralin, benzocycloheptane, substituted benzocycloheptane, wherein the substituents are selected from halogen, hydroxy, $C_{1-6}$ alkyl; or wherein $R_4$ is:

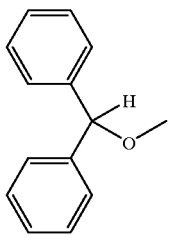

and pharmaceutically acceptable salts thereof.

2. A method of treating a human being suffering from, drug abuse, gastrointestinal disorder, hypertension, migraine, angina or depression, which comprises administering to said human a therapeutically effective amount of a compound of Formula II:

$$R_5-(HCOH)_m-(CR_2R_3)_n-N(R_6)-(CR_2R_3)_n-R_7 \qquad (II)$$

wherein m, n, $R_2$ and $R_3$ are defined as in claim 1, $R_6$ is selected from hydrogen and $C_{1-6}$ alkyl; $R_5$ and $R_7$ are each independently selected from the group consisting of; $C_{1-6}$ alkyl, substituted $C_{1-6}$ alkyl, benzyl, substituted benzyl, phenyl, substituted phenyl, benzoyl, substituted benzoyl, naphthyl, substituted naphthyl, indane, substituted indane, tetralin, substituted tetralin, benzocycloheptane, substituted benzocycloheptane, wherein the substituents are selected from $C_{1-6}$ alkyl, $C_{1-6}$ alkoxy, halogen, hydroxy, sulfo (—$SO_3H$), trifluoromethyl; or wherein $R_5$ is selected from the following:

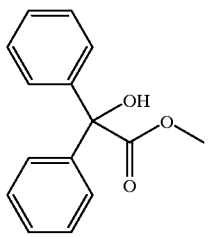 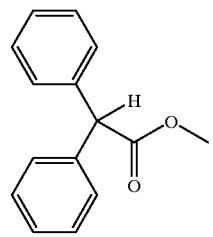

-continued

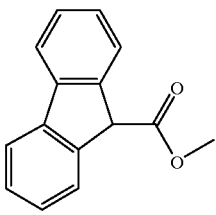

and pharmaceutically acceptable salts thereof.

3. A method of treating a human being suffering from, drug abuse, gastrointestinal disorder, hypertension, migraine, angina or depression which comprises administering to said human a therapeutically effective amount of a compound of Formula III:

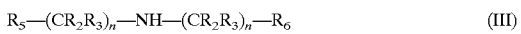

(III)

wherein n, $R_2$, $R_3$, $R_5$ and $R_6$ are defined as in claim 1 or 2; and pharmaceutically acceptable salts thereof.

4. A method of treating a human being suffering from drug abuse, gastrointestinal disorder, hypertension, migraine, angina or depression, which comprises administering to said human a therapeutically effective amount of a compound of Formula IV:

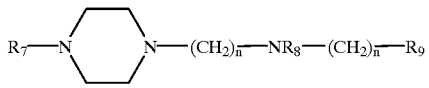

(IV)

wherein n, and m are each defined as in claim 1 or 2; $R_7$ is C1-6 alkyl, substituted C1-6 alkyl, benzyl, substituted benzyl, phenyl, substituted phenyl, benzoyl, substituted benzoyl, naphthyl, substituted naphthyl, indane, substituted indane, tetralin, substituted tetralin, benzocycloheptane, substituted benzocycloheptane; $R_8$ is selected from the group consisting of hydrogen, $C_{1-6}$ alkyl acetyl, and wherein R is selected from the group consisting of hydrogen, $C_{1-6}$ alkyl $C_{1-6}$ alkoxy, halogen, hydroxy, sulfo (—$SO_3H$), trifluoromethyl; and pharmaceutically acceptable salts thereof.

5. A method of treating a human being suffering from, drug abuse, gastrointestinal disorder, hypertension, migraine, angina or depression which comprises administering to said human a therapeutically effective amount of a compound of Formula V:

$$Ar—(CH_2)_n—(NH)_m—Het—(Ar)_m \qquad (V)$$

wherein n and m are defined as in claim 1; each Ar is independently benzyl, substituted benzyl, phenyl, substituted phenyl, naphthyl, substituted naphthyl, indane, substituted indane, tetralin, substituted tetralin, benzocycloheptane, substituted benzocycloheptane, as defined in claim 1, 2, 3, or 4, and Het is heterocyclic ring having 1 or 2 nitrogen atoms, and from 3 to 8 carbon atoms, as well as from 0 to 3 double bonds, which may likewise be further substituted with $C_{1-6}$ alkyl, $C_{1-6}$ alkylamino, hydroxy, halogen; and pharmaceutically acceptable salts thereof.

6. A method of treating a human being suffering from, drug abuse, gastrointestinal disorder, hypertension, migraine, angina or depression, which comprises administering to said human a therapeutically effective amount of a compound of Formula VI:

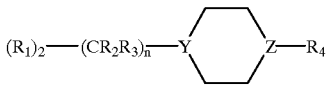

(VI)

wherein $R_1$, $R_2$, $R_3$, $R_4$ and n are each the same as defined in claim 1, or each $R_1$ may be further independently selected from

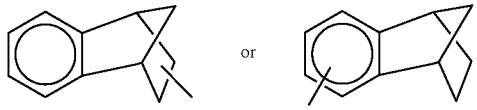

and wherein Y and Z are each independently a nitrogen or carbon; and pharmaceutically acceptable salts thereof.

7. A method of treating a human being suffering from, drug abuse, gastrointestinal disorder, hypertension, migraine, angina or depression, which comprises administering to said human a therapeutically effective amount of a compound of Formula VII:

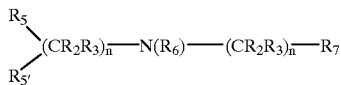

(VII)

wherein each $R_2$, $R_3$, $R_6$, $R_7$ and n are the same as defined in claim 2, and $R_5$ and $R_{5'}$ are independently hydrogen or $C_{1-6}$ alkyl, substituted $C_{1-6}$ alkyl, benzyl, substituted benzyl, phenyl, substituted phenyl, benzoyl, substituted benzoyl, 1,2,3,4-tetrahydronaphthalene, substituted 1,2,3,4-tetrahydronaphthalene, 5,6,7,8-tetrahydroisoquinoline, substituted 5,6,7,8-tetrahydroisoquinone, 1,2,3,4-tetrahydroquinoline, and substituted 1,2,3,4-tetrahydroquinoline; and pharmaceutically acceptable salts thereof.

8. A method of treating a human being suffering from a central nervous sytem disorder, drug abuse, gastrointestinal disorder, hypertension, migraine, angina or depression, which comprises administering to said human a therapeutically effective amount of one or more compounds selected from the group consisting of:
N-methyl-N-(5-phenylpentyl)-2-phenylethylamine;
N-methyl-N-(5-phenylpentyl)amine;
N-(5-phenylpentyl)-N-(2-phenylethyl)amine;
N-(5-phenylpentyl)-pyrrolidine;
N-(2-phenylethyl)-N-(l-pyrrolidinoethyl)amine;
N,N-(diphenylethyl)-N-(1-pyrrolidinoethyl)amine;
N-methyl-N-(5-(3-trifluorophenyl)pentyl)-N-(2-phenylethyl)amine;
N-methyl(5-phenylpentyl)-N-(2-(3-trifluoromethylphenyl)ethyl)amine;
N-methyl-(5-(3-trifluoromethylphenyl)-5-pentanon-1-yl)-(2-phenylethyl)amine;
N-methyl-(5-(3-trifluoromethylphenyl)-5-1-pentanol)-(2-phenylethyl)amine;
N-(2-(4-phenylsulfonic acid)ethyl-5-pentylamine;
N-diethyl-5-(1,1-diphenylpentyl)amine;
N-diethyl-5-phenyl-5-pentanon-1-yl)amine;
N-diethyl-5-(phenylpentyl)amine;
N-2-(1-phenylpropyl)-5-(phenylpentyl)amine;
N-2-(1-phenylpropyl)-4-(phenylbutyl)amine;

N-methyl-2-(1-phenylpropyl)-2-(phenylethyl)amine;
N-(5-(4-chlorophenyl)-5-pentanon-1-yl)-4-chlorophenyl) piperidine;
N-(5-(3,4-dichlorophenyl)-5-pentanon-1-yl)-4-chlorophenyl)piperidine;
N-methyl-4-(diphenylmethoxy)piperidine;
N-(5-(cyclopentyl)-5-pentanon-1-yl)piperidine;
N-(5-phenyl-5-pentanon-1-yl)piperidine;
N-5-(4-chlorophenyl)-5-pentanon-1-yl)piperidine;
N-5-(3-methoxyphenyl-5-pentyl)piperidine;
N-5-(3,4-methylenedioxyphenyl)piperidine;
N-2-(4-biphenyl)ethylpiperidine;
N-(4-phenylbutyl)-4-benzylpiperidine;
N-benzyl-4-(4-phenylbutyl)piperidine;
N-(4-phenylbutyl)-4-benzoylpiperidine;
N-(4-phenylbutyl)-4-(hydroxyphenylmethyl)piperidine;
N-4-(phenylbutyl)-4-(diphenylmethyl)piperidine;
N-phenyl-4-(3-benzoylaminopropyl)piperazine;
N-phenyl-4-(3-(p-chlorobenzoyl)aminopropyl)piperazine;
N-phenyl-4-(3-(p-methoxybenzoyl)aminopropyl) piperazine;
N-phenyl-4-(3-benzylaminopropyl)piperazine;
and N-phenyl-4-(3-benzyl-(N'-acetyl)-aminopropyl) piperazine; and pharmaceutically acceptable salts thereof.

9. A method of treating a human being suffering from drug abuse, gastrointestinal disorder, hypertension, migraine, angina or depression which comprises administering to said human a therapeutically effective amount of one or more compounds selected from the group consisting of:
N-methyl-N-(5-phenylpentyl)-2-phenylethylamine;
N-methyl-N-(5-phenylpentyl)amine;
N-(5-phenylpentyl)-N-(2-phenylethyl)amine;
N-(5-phenylpentyl)pyrrolidine;
N-(2-phenylethyl)-N-(1-pyrrolidino)amine;
N,N,-(di-2-phenylethyl)-N-(1-pyrrolidinoethyl)amine;
N-methyl-N-(5-(3-trifluorophenyl)pentyl)-N-(2-phenylethyl)amine;
N-methyl(5-phenylpentyl)-N-(2-(3-trifluoromethylphenyl)ethyl)amine;
N-methyl-(5-(3-trifluoromethylphenyl)-5-pentanon-1-yl)-(2-phenylethyl)amine;
N-methyl-(5-(3-trifluoromethylphenyl)-5-1-pentanol)-(2-phenylethyl)amine;
N-(2-(4-phenylsulfonic acid)ethyl-5-pentylamine;
N-diethyl-5-(1,1-diphenylpentyl)amine;
N-diethyl-5-phenyl-5-pentanon-1-yl)amine;
N-diethyl-5-(phenylpentyl)amine;
N-2-(1-phenylpropyl)-5-(phenylpentyl)amine;
N-2-(1-phenylpropyl)-4-(phenylbutyl)amine;
N-methyl-2-(1-phenylpropyl)-2-(phenylethyl)amine;
N-(5-(4-chlorophenyl)-5-pentanon-1-yl)-4-chlorophenyl) piperidine;
N-(5-(3,4-dichlorophenyl)-5-pentanon-1-yl)-4-chlorophenyl)piperidine;
N-methyl-4-(diphenylmethoxy)piperidine;
N-(5-(cyclopentyl)-5-pentanon-1-yl)piperidine;
N-(5-phenyl-5-pentanon-1-yl)piperidine;
N-5-(4-chlorophenyl)-5-pentanon-1-yl)piperidine;
N-5-(3-methoxyphenyl-5-pentyl)piperidine;
N-5-(3,4-methylenedioxyphenyl)piperidine;
N-2-(4-biphenyl)ethyl piperidine;
N-(4-phenylbutyl)-4-benzylpiperidine;
N-benzyl-4-(4-phenylbutyl)piperidine;
N-(4-phenylbutyl)-4-benzoylpiperidine;
N-(4-phenylbutyl)-4-(hydroxyphenylmethyl)piperidine;
N-4-(phenylbutyl)-4-(diphenylmethyl)piperidine;
N-phenyl-4-(3-benzoylaminopropyl)piperazine;

N-phenyl-4-(3-(p-chlorobenzoyl)aminopropyl)piperazine;
N-phenyl-4-(3-(p-methoxybenzoyl)aminopropyl) piperazine;
N-phenyl-4-(3-benzylaminopropyl)piperazine;
and N-phenyl-4-(3-benzyl-(N'-acetyl)-aminopropyl) piperazine; and pharmaceutically acceptable salts of said compounds.

10. A method for treating a neurological disorder comprising administering to a subject suffering from or susceptible to such a disorder an effective amount of a compound of the following formula:

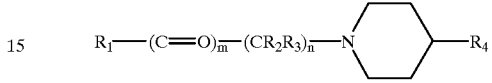

wherein m is 0 or 1; n is 0, 1, 2, 3, 4, 5, or 6; $R_1$ is selected from $C_{1-6}$ alkyl, $C_{3-6}$ cycloalkyl, phenyl, substituted phenyl, wherein the substituents are selected from $C_{1-6}$ alkyl, $C_{1-6}$ alkoxy, halogen, hydroxy, $C_{1-6}$ alkyl, trifluoromethyl;

or wherein $R_1$ is:

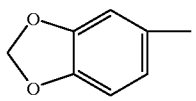

$R_2$ and $R_3$ are each independently selected from hydrogen, hydroxy, $C_{1-6}$ alkyl, or together two $R_2$ and $R_3$ groups may be a double bond between adjacent carbon atoms; $R_4$ is hydrogen, $C_{1-6}$ alkyl, substituted $C_{1-6}$ alkyl, benzyl, $C_{2-6}$ alkaryl, benzoyl, phenyl, substituted phenyl, wherein the substituents are selected from halogen, hydroxy, $C_{1-6}$ alkyl;

or wherein $R_4$ is:

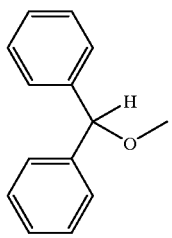

and pharmaceutically acceptable salts thereof.

11. A method for treating a neurological disorder comprising administering to a subject suffering from or susceptible to such a disorder an effective amount of a compound of the following formula:

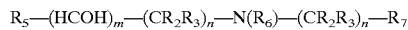

wherein m, n, $R_2$ and $R_3$ are defined as in claim 10, $R_6$ is selected from hydrogen and $C_{1-6}$ alkyl;

$R_5$ and $R_6$ are each independently selected from the group consisting of; $C_{1-6}$ alkyl, substituted $C_{1-6}$ alkyl, benzyl, substituted benzyl, phenyl, substituted phenyl, benzoyl, substituted benzoyl, wherein the substituents are selected from $C_{1-6}$ alkyl, $C_{1-6}$ alkoxy, halogen, hydroxy, sulfo (—$SO_3H$), trifluoromethyl;

or wherein $R_5$ is selected from the following:

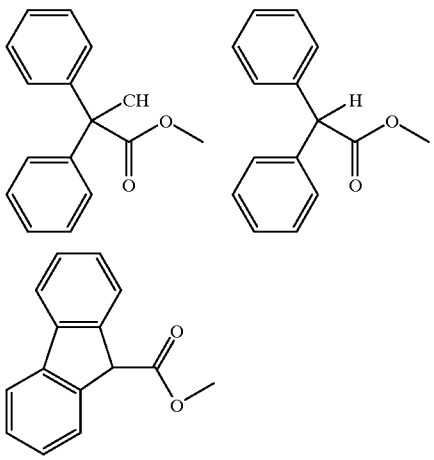

and pharmaceutically acceptable salts thereof.

12. A method for treating a neurological disorder comprising administering to a subject suffering from or susceptible to such a disorder an effective amount of a compound of the following formula:

wherein n, $R_2$, $R_3$, $R_5$ and $R_6$ are defined as in claim 10 or 11; and pharmaceutically acceptable salts thereof.

13. A method for treating a neurological disorder comprising administering to a subject suffering from or susceptible to such a disorder an effective amount of a compound of the following formula:

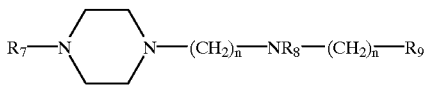

wherein n, m and $R_7$ are each defined as in claim 10 or 11; $R_8$ is selected from the group consisting of hydrogen, $C_{1-6}$ alkyl, acetyl; and wherein $R_9$ is selected from the group consisting of; hydrogen, $C_{1-6}$ alkyl, substituted $C_{1-6}$ alkyl, benzyl, substituted benzyl, phenyl, substituted phenyl, benzoyl, substituted benzoyl, wherein the substituents are selected from $C_{1-6}$ alkyl, $C_{1-6}$ alkoxy, halogen, hydroxy, sulfo (—$SO_3H$), trifluoromethyl; and pharmaceutically acceptable salts thereof.

14. A method for treating a neurological disorder comprising administering to a subject suffering from or susceptible to such a disorder an effective amount of a compound of the following formula:

wherein n and m are defined as in claim 10 or 11; each Ar is independently benzyl, substituted benzyl, phenyl or substituted phenyl (as defined above), and Het is heterocyclic ring having 1 or 2 nitrogen atoms, and from 3 to 8 carbon atoms, as well as from 0 to 3 double bonds, which may likewise be further substituted with $C_{1-6}$ alkyl, $C_{1-6}$ alkylamino, hydroxy, halogen; and pharmaceutically acceptable salts thereof.

15. A method for treating a neurological disorder comprising administering to a subject suffering from or susceptible to such a disorder an effective amount of a compound of the following formula:

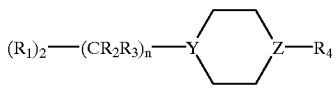

wherein $R_1$, $R_2$, $R_3$, $R_4$ and n are each the same as defined in claim 10 or 11, or each $R_1$ may be further independently selected from

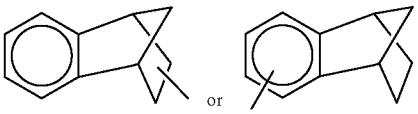

and wherein Y and Z are each independently a nitrogen or carbon; and pharmaceutically acceptable salts thereof.

16. A compound of the following Formula VII:

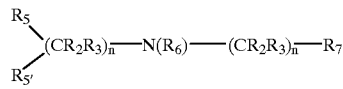

wherein $R_2$, $R_3$, $R_6$, and $R_7$ are the same as defined in claim 10 or 11, n is from 1, 2, 3, 4, 5, or 6, and $R_5$ and $R_{5'}$ are independently hydrogen or $C_{1-6}$ alkyl, substituted $C_{1-6}$ alkyl, benzyl, substituted benzyl, phenyl, substituted phenyl, benzoyl, substituted benzoyl, 1,2,3,4-tetrahydronaphthalene, substituted 1,2,3,4-tetrahydronaphthalene, 5,6,7,8-tetrahydroisoquinoline, substituted 5,6,7,8-tetrahydroisoquinoline, 1,2,3,4-tetrahydroquinoline, and substituted 1,2,3,4-tetrahydroquinoline; and pharmaceutically acceptable salts thereof.

17. A method for treating a neurological disorder comprising administering to a subject suffering from or susceptible to such a disorder an effective amount of a compound selected from the group consisting of:
N-methyl-N-(5-phenylpentyl)-2-phenylethylamine;
N-methyl-N-(5-phenylpentyl)amine;
N-(5-phenylpentyl)-N-(2-phenylethyl)amine;
N-(5-phenylpentyl)pyrrolidine;
N-(2-phenylethyl)-N-(1-pyrrolidino)amine;
N,N,-(di-2-phenylethyl)-N-(1-pyrrolidinoethyl)amine;
N-methyl-N-(5-(3-trifluorophenyl)pentyl)-N-(2-phenylethyl)amine;
N-methyl(5-phenylpentyl)-N-(2-(3-trifluoromethylphenyl)ethyl)amine;
N-methyl-(5-(3-trifluoromethylphenyl)-5-pentanon-1-yl)-(2-phenylethyl)amine;
N-methyl-(5-(3-trifluoromethylphenyl)-5-1-pentanol)-(2-phenylethyl)amine;
N-(2-(4-phenylsulfonic acid)ethyl-5-pentylamine;
N-diethyl-5-(1,1-diphenylpentyl)amine;
N-diethyl-5-phenyl-5-pentanon-1-yl)amine;
N-diethyl-5-(phenylpentyl)amine;
N-2-(1-phenylpropyl)-5-(phenylpentyl)amine;
N-2-(1-phenylpropyl)-4-(phenylbutyl)amine;
N-methyl-2-(1-phenylpropyl)-2-(phenylethyl)amine;
N-(5-(4-chlorophenyl)-5-pentanon-1-yl)-4-chlorophenyl)piperidine;
N-(5-(3,4-dichlorophenyl)-5-pentanon-1-yl)-4-chlorophenyl)piperidine;
N-methyl-4-(diphenylmethoxy)piperidine;

N-(5-(cyclopentyl)-5-pentanon-1-yl)piperidine;
N-(5-phenyl-5-pentanon-1-yl)piperidine;
N-5-(4-chlorophenyl)-5-pentanon-1-yl)piperidine;
N-5-(3-methoxyphenyl-5-pentyl)piperidine;
N-5-(3,4-methylenedioxyphenyl)piperidine;
N-2-(4-biphenyl)ethyl piperidine;
N-phenyl-4-(3-benzoylaminopropyl)piperazine;
N-phenyl-4-(3-(p-chlorobenzoyl)aminopropyl)piperazine;
N-phenyl-4-(3-(p-methoxybenzoyl)aminopropyl) piperazine;
N-phenyl-4-(3-benzylaminopropyl)piperazine;
and N-phenyl-4-(3-(N'-acetyl)-benzylaminopropyl) piperazine; and pharmaceutically acceptable salts thereof.

* * * * *